US012714810B2

(12) United States Patent
Luo

(10) Patent No.: US 12,714,810 B2
(45) Date of Patent: Aug. 25, 2026

(54) NOISE-REDUCING GAS PASSAGE DEVICE WITH A RESONANT CHAMBER

(71) Applicant: WALLENBERG UNION LLC, Newark, DE (US)

(72) Inventor: David Luo, Newark, DE (US)

(73) Assignee: WALLENBERG UNION LLC, Newark, DE (US)

( * ) Notice: Subject to any disclaimer, the term of this patent is extended or adjusted under 35 U.S.C. 154(b) by 16 days.

(21) Appl. No.: 18/785,025

(22) Filed: Jul. 26, 2024

(65) Prior Publication Data

US 2026/0027312 A1 Jan. 29, 2026

(51) Int. Cl.
*A61M 16/00* (2006.01)

(52) U.S. Cl.
CPC ..... *A61M 16/0066* (2013.01); *A61M 2205/42* (2013.01)

(58) Field of Classification Search
CPC ................ A61M 16/00–0084; A61M 2205/42
See application file for complete search history.

(56) References Cited

U.S. PATENT DOCUMENTS 6,698,390 B1 * 3/2004 Kostun .............. F02M 35/1266 181/241
7,328,586 B2 * 2/2008 Gau ........................ F24F 13/24 62/158
9,790,937 B2 * 10/2017 Morrison ............ F04B 39/0066
9,855,397 B2 * 1/2018 Peake ............... A61M 16/0875
10,760,537 B2 * 9/2020 Kimura ..................... E04B 1/84
12,115,309 B2 * 10/2024 Liu .................. A61M 16/1075
2002/0134378 A1 * 9/2002 Finnegan ............ A61M 16/021 128/200.24
2007/0169781 A1 * 7/2007 Tang ..................... A61M 16/00 128/205.25
2008/0257346 A1 * 10/2008 Lathrop ............ A61M 16/0066 181/224
2012/0121441 A1 * 5/2012 Morrison ............ F04B 39/0066 417/63
2014/0299406 A1 * 10/2014 Librett .............. A61M 16/0858 181/224
2020/0038606 A1 * 2/2020 Wada ................ A61M 16/0066
2021/0393914 A1 * 12/2021 Tsuji ................. A61M 16/0003
2023/0233780 A1 * 7/2023 Zhi .................. A61M 16/0066
2023/0398318 A1 * 12/2023 Mazzone .......... A61M 16/0066

* cited by examiner

*Primary Examiner* — Joseph D. Boecker
*Assistant Examiner* — Thomas W Greig
(74) *Attorney, Agent, or Firm* — Birch, Stewart, Kolasch & Birch, LLP

(57) ABSTRACT

A noise-reducing gas passage device with a resonant chamber, including a casing with an air intake and air outlet, which forms the resonant chamber and other chambers other than the resonant chamber. The other chambers may consist of a single chamber or multiple chambers. The other chambers including multiple chambers have a first chamber and a second chamber. The resonant chamber serves as the primary noise-reducing structure within the gas passage device, configured to be a cavity formed by the interior space of the casing. The noise-reducing structure also includes a neck, configured to communicate the resonant chamber with the other chambers, facilitating the transmission of sound waves into the resonant chamber for energy conversion. By controlling the position of the resonant chamber and the parameters of both the resonant chamber and the neck, maximal noise reduction in the noise-reducing gas passage is achieved.

25 Claims, 16 Drawing Sheets

NOISE-REDUCING GAS PASSAGE DEVICE WITH A RESONANT CHAMBER

TECHNICAL FIELD

This disclosure relates to a noise-reducing gas passage device having a resonant chamber configured to attenuate noise generated by the gas entering the device, providing patients with a more comfortable sleep and treatment environment.

BACKGROUND

In the increasingly rapidly developing modern society, people's pace of life is getting faster, leading to irregular habits such as unhealthy eating, lack of exercise, and excessive work, which contribute to rising obesity rates. The aging population is another significant issue that cannot be ignored, and these factors can cause and exacerbate sleep-related breathing disorders. Mild conditions like snoring can emerge, but without improvements in lifestyle or treatment, mild sleep-related breathing disorders can progress into more severe conditions such as obstructive sleep apnea.

Studies show that habitual snoring prevalence in European populations is between 15.6% and 19%, with occasional snoring at 26% to 30%. In Japan, the prevalence of snoring disorders is between 12.8% and 16.0%, while surveys in China indicate a prevalence of about 13%, increasing with age. Among people aged 60 to 69, the prevalence is 39% in men and 17% in women. Using the Apnea-Hypopnea Index (AHI) with a threshold of greater than or equal to 5 to diagnose obstructive sleep apnea syndrome (OSAS), the prevalence statistics for OSAS show a sensitivity of 70.8% and a specificity of 47.7%. In the US, the prevalence among men over 40 is 1.24%, in European countries, it ranges from 1% to 2.7%, and in Japan, it ranges from 1.3% to 4.2%, with 14% of men and 5% of women suffering from OSAS, and the numbers are rising. Globally, a significant number of people suffer from sleep-related breathing disorders, and among those with mild conditions like snoring, there is an increasing prevalence of more severe conditions such as sleep apnea. This thus underscores the importance of sleep apnea as a worthy area of research. In modern society, mainstream treatments for sleep apnea include wearing various orthotic devices, oxygen therapy, medication, using home ventilators, and lifestyle and behavioral changes. In some implementations, surgical interventions are also considered. Among these, non-surgical treatments, particularly treatment with home ventilators or Continuous Positive Airway Pressure (CPAP) therapy, are regarded as the most popular and effective. This is mainly because Positive Airway Pressure (PAP) therapy is a non-invasive, safe, and effective treatment method that can quickly improve a patient's sleep quality and life quality. The development of home ventilators has introduced smarter devices such as CPAP, BiPAP, and APAP, which can autonomously adjust the continuous positive pressurized gas delivered to the patient's airway. As demand for home ventilators grows, providing patients with more effective and efficient devices is a key challenge for developers.

The principle of the ventilator involves using an internal blower to provide a continuous pressurized airflow, which is then delivered through a hose to the patient's nose or mouth to at least one airway, maintaining clear airways and preventing airway blockage caused by muscle relaxation and the collapse of soft tissues in the throat during supine sleep. This can lead to sleep-related breathing disorders such as sleep apnea. In this process, a key component inside the ventilator is its airway, which not only provides space to accommodate the blower but also features various structures and/or noise-reducing components to minimize noise, ensuring a quiet sleeping environment and enhancing the effectiveness of the treatment.

SUMMARY

The objective of this disclosure is to provide a noise-reducing gas passage device with a resonant chamber, which through structural improvements in the noise-reducing passage achieves an appropriate noise level, ensuring patient health and safety. This design facilitates the manufacturing of noise-reducing gas passage devices within respiratory-related machines and enables the gas passage device to quickly adapt to the market. The noise-reducing gas passage device with a resonant chamber can be used by patients over long periods and extended phases, overcoming the limitations present in existing technologies used in similar products. Thus, it offers a more effective solution with broader application scenarios and spaces, supplying a continuous positive airway pressurized airflow in a safer manner to treat sleep-related breathing disorders.

The disclosure discussed herein provides a noise-reducing gas passage device that includes a resonant chamber, configured to generate pressurized gas and continuously deliver it to a patient's respiratory tract. The noise-reducing gas passage device includes:

a casing that is configured to include at least two chambers that have at least one resonant chamber, an air intake, and an air outlet. The air intake is configured to receive gas, and the air outlet is configured to exhaust the pressurized gas; and the at least one resonant chamber, which has walls surrounding it, with at least one wall of the at least one resonant chamber including at least one opening to communicate with other chambers other than the resonant chamber;

When the noise-reducing gas passage device is operational, the gas flows in the at least two chambers other than the resonant chamber without substantially entering the at least one resonant chamber. Additionally, the volume of the at least one resonant chamber is less than or equal to the combined volume of the at least two chambers other than the resonant chamber.

In an embodiment, the at least one resonant chamber is positioned at an edge portion of the casing of the noise-reducing gas passage device.

In an embodiment, the noise-reducing gas passage device also includes a blower that provides the pressurized gas, and the at least two chambers other than the resonant chamber include a first chamber to house the blower and a second chamber separable from the first chamber.

In an embodiment, there is a height difference between a central point of at least one of the first chamber and the second chamber and a central point of the resonant chamber.

In an embodiment, a distance between the central point of the at least one resonant chamber and the central point of the first chamber is greater than a distance between the central point of the first chamber and the central point of the second chamber.

In an embodiment, the at least one resonant chamber is configured to be at least partially integrally formed with the casing.

Another noise-reducing gas passage device is provided. The noise-reducing gas passage device includes a resonant chamber, configured to generate pressurized gas and continuously deliver it to a patient's respiratory tract. The noise-reducing gas passage device includes:

a casing that is configured to include at least two chambers that have at least one resonant chamber, an air intake, and an air outlet. The air intake is configured to receive gas, and the air outlet is configured to exhaust the pressurized gas; and the at least one resonant chamber, which has walls surrounding it, with at least one wall having at least one opening to communicate with other chambers other than the at least one resonant chamber;

The communication between the at least one resonant chamber and the other chambers other than the at least one resonant chamber is formed by a neck, which has a first end part connectable to the at least one opening of the at least one resonant chamber and a second end part connectable to the other chambers other than the at least one resonant chamber. Additionally, the ratio of the height of the neck to the height of the resonant chamber is at least 1:300.

In an embodiment, the noise-reducing gas passage device includes a blower that is configured to provide the pressurized gas, wherein the blower is provided within the other chambers other than the at least one resonant chamber, and wherein an axis of the blower is parallel to a central line of the neck.

In an embodiment, the noise-reducing gas passage device includes multiple resonant chambers.

In an embodiment, cross-sections of the neck are the same at a same angle from the first end part to the second end part.

In an embodiment, the noise-reducing gas passage device includes multiple necks to communicate the at least one resonant chamber with the other chambers other than the at least one resonant chamber.

In an embodiment, the casing of the noise-reducing gas passage device includes one of the one of the following materials: polypropylene, polycarbonate, poly(ethylene terephthalate)-1,4-cyclohexanedimethanol ester, polyamide, or polyetheretherketone.

The disclosure further provides a noise-reducing gas passage device that includes a resonant chamber, configured to generate pressurized gas and continuously deliver it to a patient's respiratory tract. The noise-reducing gas passage device includes:

a casing that features at least two chambers that have at least one resonant chamber, an air intake, and an air outlet. The air intake is configured to receive gas, and the air outlet is designed to exhaust the pressurized gas; and the at least one resonant chamber, which has walls surrounding it, with at least one wall having at least one opening to communicate with other chambers other than the at least one resonant chamber;

The communication between the at least one resonant chamber and the other chambers other than the at least one resonant chamber is formed by a neck, which has a first end part connectable to the at least one opening of the at least one resonant chamber and a second end part connectable to the other chambers other than the at least one resonant chamber. The airflow within the other chambers other than the at least one resonant chamber forms a main airflow path, and the angle between a tangent of the main airflow path at the second end part and a central line of the neck is equal to or greater than 30°.

In an embodiment, the walls of the at least one resonant chamber include one or more of the following materials: plastic, foam, silicone.

In an embodiment, a cross-section of the neck is circular or elliptical.

In an embodiment, a diameter of the circular cross-section of the neck or a major axis of the elliptical cross-section of the neck is equal to or greater than 0.5 mm.

In an embodiment, an area of the cross-section of the neck is at least 0.19625 $mm^2$.

In an embodiment, the other chambers other than the at least one resonant chamber include a noise-reducing component.

In an embodiment, a form of the noise-reducing component is such that the other chambers other than the at least one resonant chamber have multiple walls of a same form spaced at a certain distance apart.

In an embodiment, a material of the walls of the at least one resonant chamber includes a rigid material.

The disclosure further provides a noise-reducing gas passage device that includes a resonant chamber, configured to generate pressurized gas and continuously deliver it to a patient's respiratory tract. The noise-reducing gas passage device includes:

a casing that is configured to include at least two chambers that have at least one resonant chamber, an air intake, and an air outlet. The air intake is configured to receive gas, and the air outlet is configured to exhaust the pressurized gas; and the at least one resonant chamber, which has walls surrounding it, with only one of the walls having at least one opening to communicate with other chambers other than at least one resonant chamber;

The communication between the at least one resonant chamber and the other chambers other than at least one resonant chamber is formed by a neck, which has a first end part connectable to the at least one opening of the at least one resonant chamber and a second end part connectable to the other chambers other than at least one resonant chamber.

In an embodiment, the neck is formed by a wall thickness at a connection point between the at least one resonant chamber and the other chambers other than the at least one resonant chamber.

In an embodiment, a total volume of the at least one resonant chamber is greater than or equal to 785 $mm^3$.

In an embodiment, the noise-reducing gas passage device includes multiple resonant chambers, and the multiple resonant chambers are provided at different locations.

In an embodiment, the walls of the at least one resonant chamber include one of the following materials: polypropylene, polycarbonate, poly(ethylene terephthalate)-1,4-cyclohexanedimethanol ester, polyamide, or polyetheretherketone.

In an embodiment, an area of the at least one opening of the at least one resonant chamber is greater than or equal to 0.19625 $mm^2$.

Implementing the noise-reducing gas passage device with a resonant chamber as described in this disclosure provides several beneficial effects:

1. The integration of the resonant chamber with the noise-reducing gas passage device offers an innovative noise reduction structure to the ventilator market that is highly efficient and reliable. The design of the resonant chamber is inspired by muffler technology, which is supported by reliable computational models. Experimental validation of this disclosure has confirmed that this resonant chamber structure is suitable for use in ventilators and noise-reducing gas passage devices in other related machines, where it can significantly reduce noise levels. The technology, based on the principles of sound wave resonance and negative pressure, efficiently dissipates and absorbs sound waves at specific frequencies. This noise-canceling mechanism is particularly crucial in the presence of high-noise sources such as blowers within the noise-reducing gas passage devices. This disclosure not only applies traditional noise cancellation technology to ventilators but also thoroughly considers the airflow dynamics and acoustic characteristics within respiratory machines, integrating them closely with the noise-reducing gas passage devices. Through in-depth research and precise design and adjustment of the resonant chamber and neck parameters, a superior noise reduction effect can be achieved, providing patients with a quieter and more comfortable usage environment. As patients' demand for high-quality, low-noise respiratory products continues to grow, respiratory products employing this noise reduction technology can meet market needs effectively.

2. This disclosure introduces a resonant chamber as a new and simple noise reduction structure that not only effectively reduces noise but also offers several advantages over traditional foam used within chambers of noise-reducing gas passage devices. These advantages include: (1) In 2021, a prominent international brand issued its first global recall affecting some of its Bi-level Positive Airway Pressure (BiPAP) devices, Continuous Positive Airway Pressure (CPAP) devices, and mechanical ventilators, and subsequent recalls were also issued, primarily due to the noise-reducing foam used inside the noise-reducing gas passage devices. The U.S. Food and Drug Administration (FDA) requires ventilators to achieve a noise level below 30 dB to receive marketing approval. Currently, using foam for noise reduction is the simplest method because foam materials are readily available and easy to manufacture. Foam's unique porous structure and material properties enable it to convert noise into minimal energy, effectively achieving significant noise reduction. Placing foam within the noise-reducing gas passage device is a common, simple, and effective way to meet these regulatory noise level requirements. This method is widely used due to its straightforward implementation that allows for effective sound absorption. However, foam has several potential disadvantages related to human health and can pose environmental hazards. These include: a. Foam is typically made from synthetic materials that may contain chemical additives. These chemicals can leach out as the foam ages and degrades, potentially increasing the health risks to patients over time. In contrast, the innovative noise-reducing structure proposed by this disclosure, which can be integrally formed with the casing of the noise-reducing gas passage device, does not pose the same hazards associated with foam. b. Due to its soft and relatively loose surface, foam can be worn away or peeled off by airflow, releasing particles. These particles can enter the patient's respiratory tract with the airflow, potentially causing irritation and respiratory issues such as throat pain and coughing, particularly in individuals with pre-existing conditions like asthma or Chronic Obstructive Pulmonary Disease (COPD). c. Foam can accumulate dust, bacteria, and other contaminants over time. Particularly in respiratory machines, foam is not easily washable and moisture from breath can promote bacterial growth and infection risks. To prevent these issues, particularly in the design of respiratory-related machines, it is crucial to avoid using materials that can generate particulate matter. d. Due to the components of foam, the production and recycling processes of foam generate certain harmful gases. The resonant chamber structure in the noise-reducing gas passage device offers efficient noise reduction capabilities, which means that the use of foam materials can be reduced in these devices, thereby decreasing the respiratory machine market's reliance on and use of foam materials. This alternative approach not only meets the urgent needs of modern society for environmental protection and sustainable development but also aligns with the overall goals of green development. (2) Using the effective noise-reduction structure of this disclosure instead of foam can extend the lifespan of respiratory-related machines. Foam is typically made from synthetic materials like polyurethane and polyether, which are more susceptible to environmental influences, resulting in a shorter lifespan compared to materials like plastic or silicone. In contrast, devices with a resonant chamber for noise-reducing gas passage device achieve regulatory noise levels without the extensive use of foam within the chamber, enhancing the device's durability. Additionally, noise-reducing gas passage devices without internal foam do not require complex structures to secure foam, simplifying the internal structure and reducing complexity, which helps to further improve the reliability and stability of the device. (3) As the market for respiratory-related machines grows, more patients have varying preferences and needs. Some patients prioritize health and safety and may opt for noise-reducing gas passage devices that do not contain internal foam, while others who have higher noise sensitivity may prefer devices that ensure a quieter environment. Therefore, considering individual needs and preferences, and under the premise of ensuring safety, soundproofing materials (including silicone, gel, and small amounts of foam that can isolate or absorb noise) may be added to the chambers of noise-reducing gas passage devices to achieve lower noise levels. Soundproofing materials include foam, silicone, and other soft materials. Adding foam within the chambers of devices with a resonant chamber can further reduce noise and offer more options to patients. This flexible design approach provides a more personalized and considerate respiratory treatment experience, further enhancing patients' sleep quality and life quality.

3. The structure is simple and cost-effective, making it a more economical choice. The requirements for the resonant chamber are merely a chamber surrounded by walls, with at least one wall including at least one neck (or opening). This structure is simpler and more straightforward compared to the noise reduction structures in noise-reducing gas passage devices currently available on the market. The simplicity of the resonant chamber's design not only makes it more streamlined but also easier to manufacture and assemble. This means that noise-reducing gas passage devices with a resonant chamber are easier to produce than existing noise-reducing structures in noise-reducing gas passage devices, with reduced process and material costs during manufacturing. Therefore, although this design increases the difficulty of initial design and research, and the cost of research and development through dozens of model validations, it can effectively reduce manufacturing costs in the later stages, providing patients with an economical and efficient noise reduction solution. Additionally, a simpler structure not only means lower manufacturing costs but also enhances production efficiency, potentially shortening production cycles and further reducing overall production costs, helping to achieve widespread application in the market.

4. Highly adaptable, easy to integrate, and does not affect airflow. Due to their simple structure, the resonant chamber and neck can be easily and conveniently integrated into the structure of existing noise-reducing gas passage devices without the need for significant modifications to the existing designs, allowing minimal changes to the resonant chamber itself. This offers manufacturers greater freedom in production and design. Additionally, by adjusting parameters of the neck and the resonant chamber such as the cross-sectional area of the neck and the volume of the resonant chamber, it is possible to tailor the noise reduction more precisely for specific sound-emitting components according to their sound frequencies and requirements, fulfilling the need for customized noise reduction in different noise-reducing gas passage devices. Furthermore, since the resonant chamber essentially acts as a true cavity that with no airflow entering, primarily interacting with sound waves rather than the airflow, it influences sound waves without affecting the airflow. This means it does not impact the flow rate and pressure of the main function of the noise-reducing gas passage devices (i.e., providing airflow of specific volume and pressure). Therefore, the airflow can maintain its original specified volume and pressure when passing through the noise-reducing gas passage device with a resonant chamber. Overall, the resonant chamber structure introduced by this disclosure provides the market for respiratory-related machines with a flexible, efficient, and reliable noise reduction solution.

DETAILED DESCRIPTION

Figure 1:
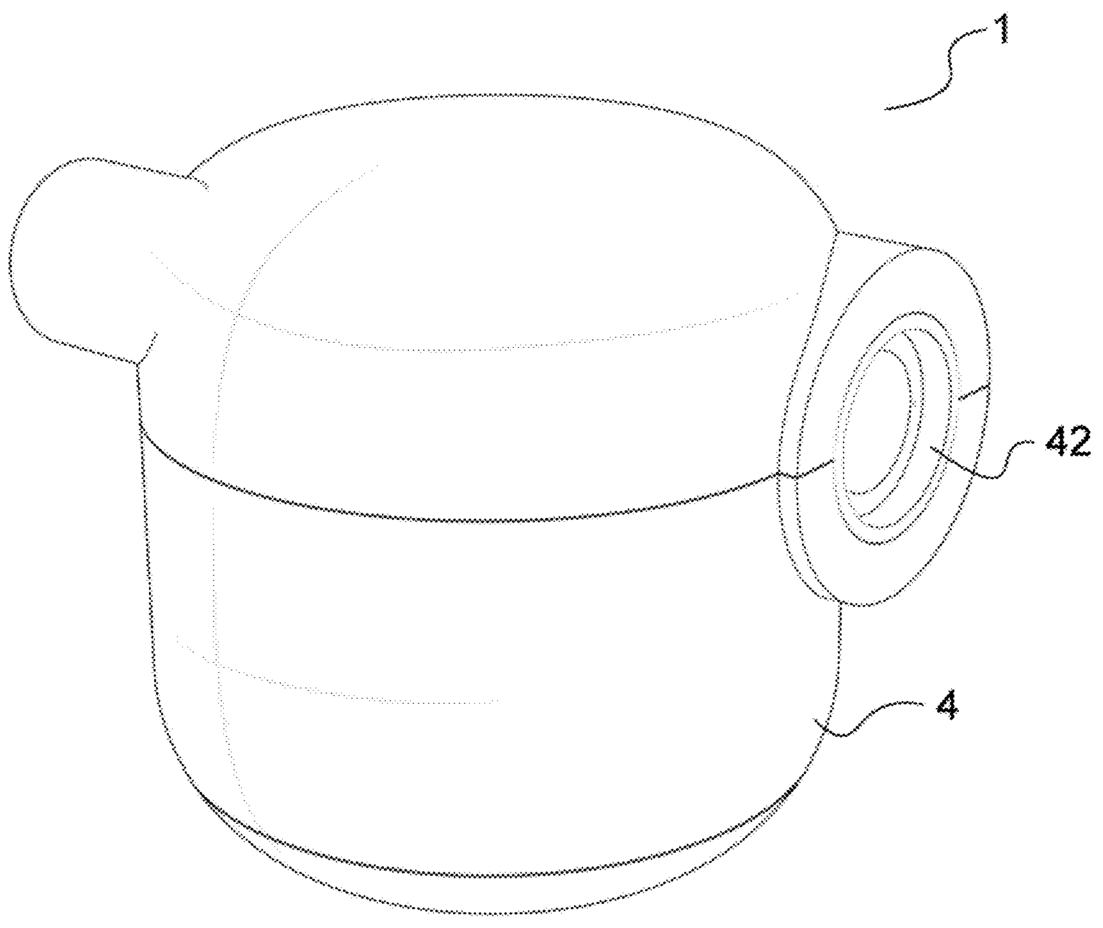
FIG. 1 shows a three-dimensional schematic diagram of a noise-reducing gas passage device with a resonant chamber in accordance with one embodiment.
Figure 2:
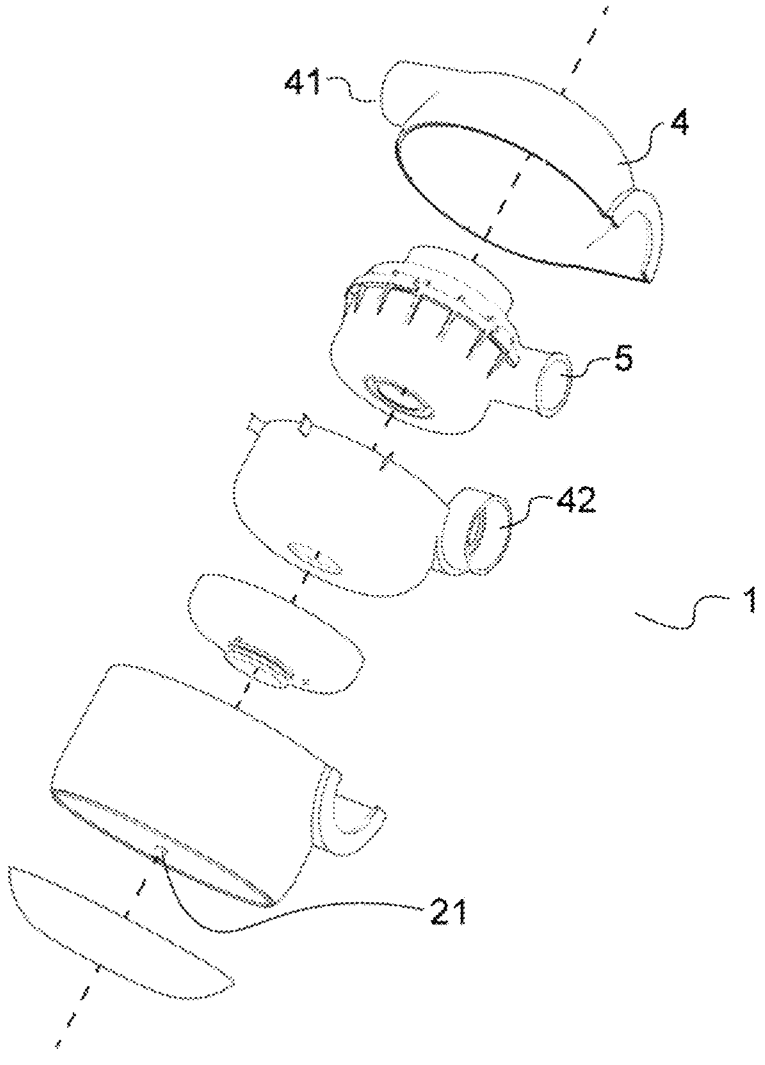
FIG. 2 shows an exploded view of the structure of a noise-reducing gas passage device with a resonant chamber in accordance with one embodiment.
Figure 3:
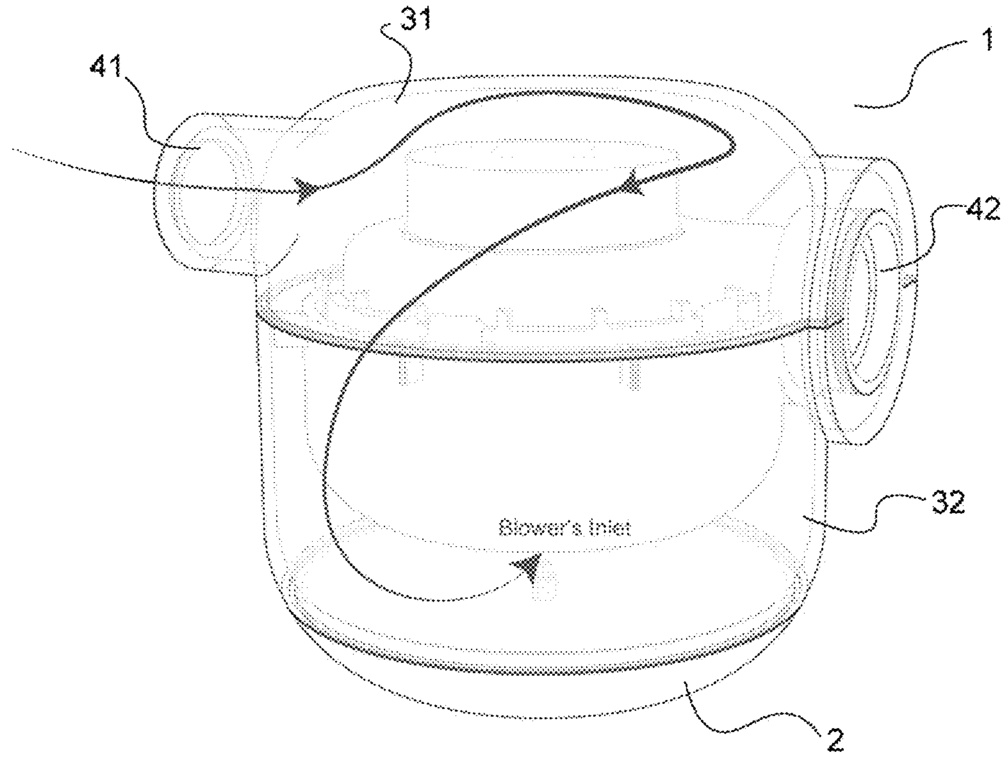
FIG. 3 shows the main airflow path of a noise-reducing gas passage device with a resonant chamber in accordance with one embodiment.

To facilitate understanding of the disclosure, a more comprehensive description will be provided with reference to the accompanying drawings, which illustrate typical embodiments of the disclosure. However, the disclosure can be implemented in many different forms and is not limited to the embodiments described herein. Instead, these embodiments are provided to make the disclosure more thorough and comprehensive.

Unless otherwise defined, all technical and scientific terms used herein have the same meaning as commonly understood by one of ordinary skill in the art to which this disclosure belongs. The terminology used in the description of the disclosure herein is for the purpose of describing particular embodiments only and is not intended to be limiting of the disclosure.

This disclosure addresses issues with existing respiratory machines, such as ventilators that use foam for noise reduction within their noise-reducing gas passage devices. Foam used in this way is prone to damage and aging, may compromise patient health and safety, and involves more complex manufacturing processes that are less environmentally friendly. The disclosure provides a safer, more reliable, and more maintenance-friendly noise-reducing gas passage device. The designed device not only optimizes various disadvantages of existing noise-reducing gas passage devices but also ensures that the overall device meets regulatory noise levels, making it a superior technological disclosure for patients, producers, and the market. This disclosure's choice to use a resonant chamber structure inside the noise-reducing gas passage device, replacing traditional foam-based noise reduction, also represents a sustainable and environmentally friendly design.

The following specific embodiments illustrate several structures of a noise-reducing gas passage device with a resonant chamber according to this disclosure.

Embodiment 1

This embodiment introduces a noise-reducing gas passage device 1 configured with a resonant chamber 2. This example provides a three-dimensional schematic diagram, an exploded structural diagram, airflow path diagram, schematic diagrams of each structural component, and data diagrams, as referenced in FIGS. 1-7. This example pertains to a noise-reducing gas passage device 1 that is configured to generate pressurized gas and continuously deliver it to a patient's respiratory tract. The device 1 includes a casing 4 that forms the chambers, which comprise the resonant chamber 2 and other chambers 3 (any chamber other than the resonant chamber 2 is referred to as other chambers). The blower 5 is placed within one of these other chambers 3. This technological disclosure effectively sets the parameters for the resonant chamber 2, its communication with the other chambers 3, and the structural data of the resonant chamber 2 to maximize its efficiency. The design of the resonant chamber 2 is based on certain principles to disperse airflow and noise, achieving a scientifically effective noise reduction outcome.

Specifically, the noise-reducing gas passage device 1 includes a casing 4 having at least two parts, configured to form internal chambers and isolate internal components (such as the blower 5 and other components provided inside the casing) from the external environment. In this disclosure, the casing 4 is configured to have at least two chambers, namely the resonant chamber 2 and other chambers 3. The casing 4 also includes an air intake 41 and an air outlet 42, where the air intake 41 and the air outlet 42 are respectively configured to receive incoming gas and expel pressurized gas. Apart from the arrangement where the resonant chamber 2 is provided inside the other chambers 3 (i.e., the resonant chamber 2 being surrounded by other chambers 3), the walls of the casing 4 are also the walls of both the resonant chamber 2 and the other chambers 3. In this embodiment, the noise-reducing gas passage device 1 further includes a blower 5 that provides pressurized gas, with the other chambers 3 comprising a first chamber 31 housing the blower 5, and a second chamber 32 separated from the first chamber 31. Thus, the noise-reducing gas passage device 1 has three chambers including the resonant chamber 2, the first chamber 31, and the second chamber 32, where the first chamber 31 and the second chamber 32 are two chambers with a vertical height difference. Furthermore, the casing 4 of the noise-reducing gas passage device 1 is made from one of the following materials: polypropylene (PP), polycarbonate (PC), poly (ethylene terephthalate)-1,4-cyclohexanedimethanol ester (PCTG), polyamide (PA), or polyetheretherketone (PEEK).

Figure 4:
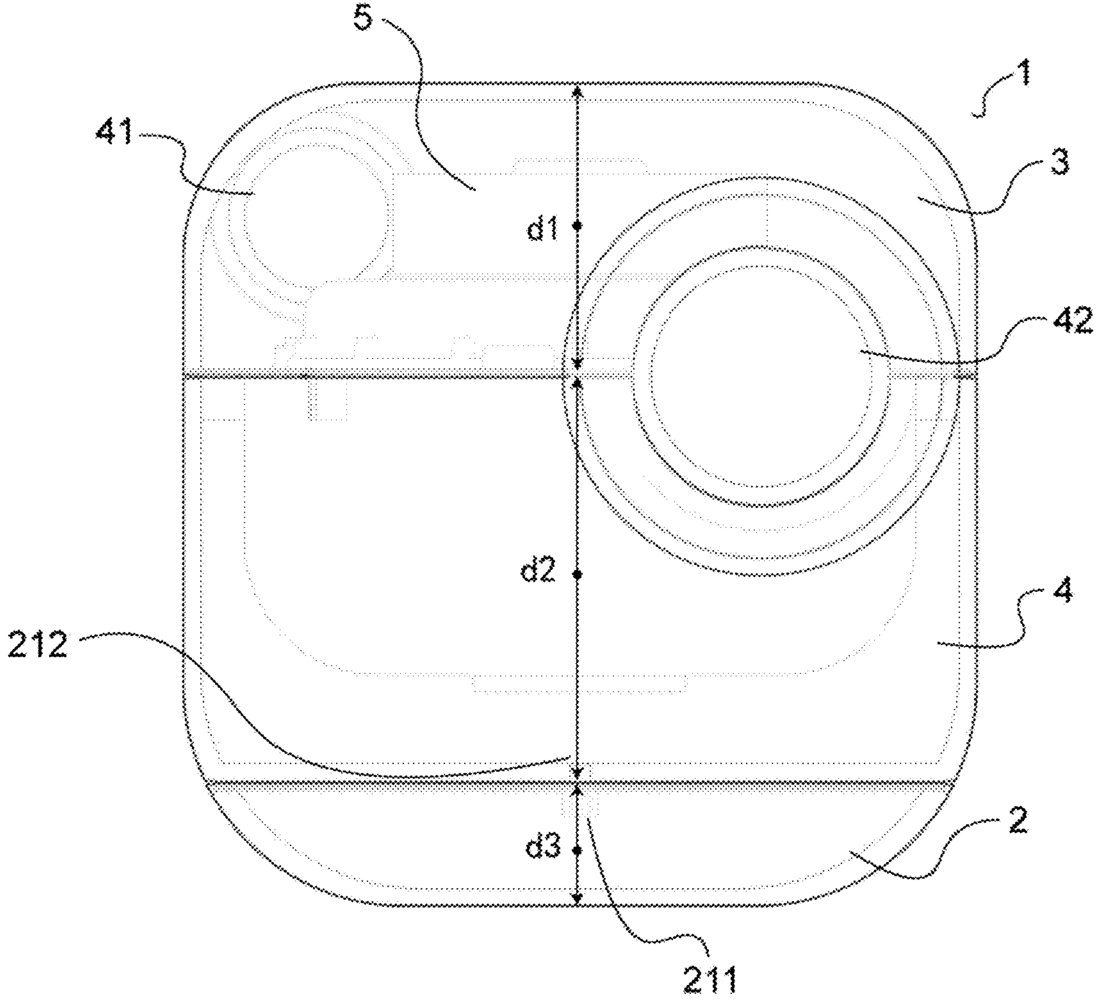
FIG. 4 shows a front view of a noise-reducing gas passage device with a resonant chamber in accordance with one embodiment.
Figure 5:
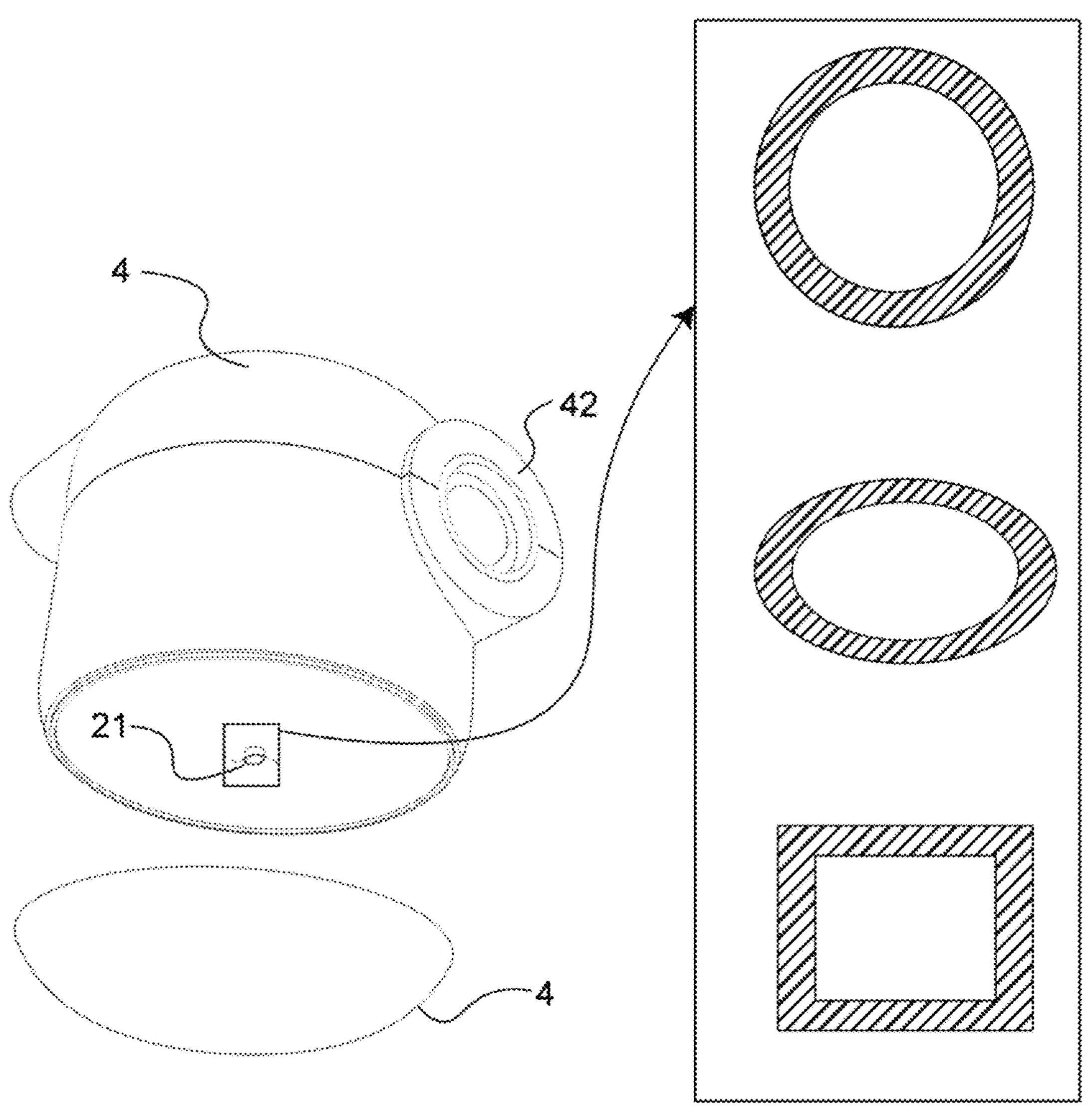
FIG. 5 shows a schematic diagram of the cross-sectional shape of the neck in a noise-reducing gas passage device with a resonant chamber in accordance with one embodiment.
Figure 6:
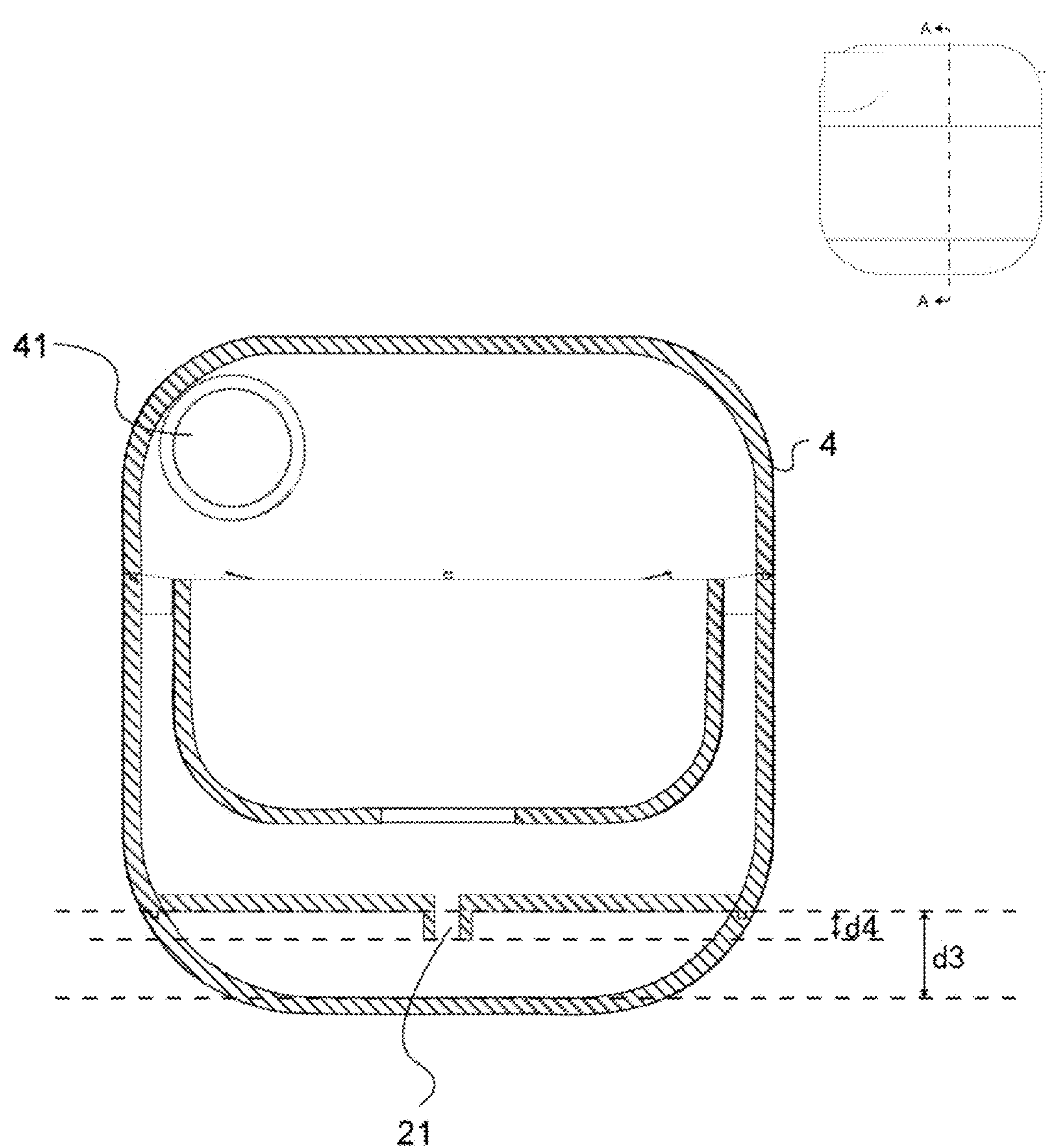
FIG. 6 shows a schematic diagram illustrating the height of the neck and the resonant chamber in a noise-reducing gas passage device in accordance with one embodiment.
Figure 7:
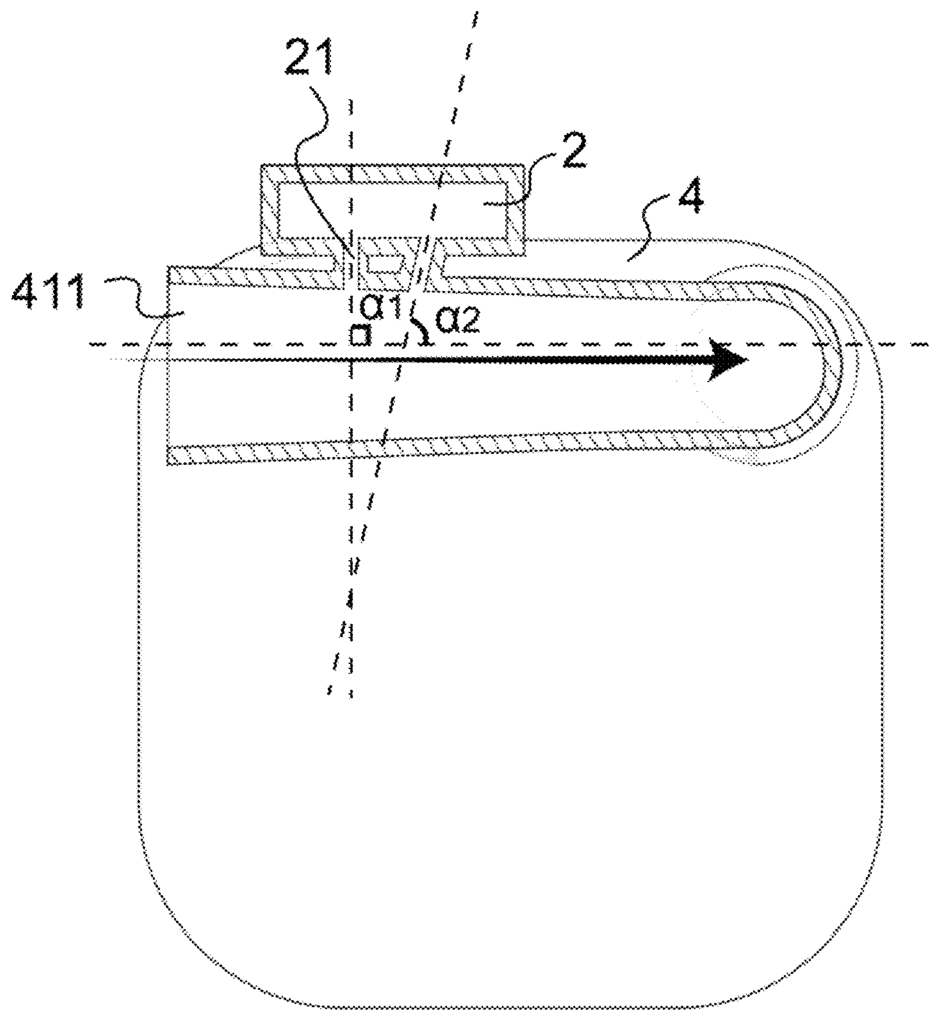
FIG. 7 shows a schematic diagram of the angle between the tangent at the second end of the main airflow path and the central line of the neck in the noise-reducing gas passage device in accordance with one embodiment.

In the disclosure discussed herein, the key component of the noise-reducing gas passage device 1 is the resonant chamber 2, which is specifically structured as a cavity formed by walls and in communication with other chambers 3. This means that the noise-reducing gas passage device 1 has at least one resonant chamber 2 with walls surrounding the chamber, where at least one wall of the chamber has at least one opening configured to communicate with other chambers 3. The walls of the resonant chamber 2 include one or more materials such as plastic, foam, or silicone. In this embodiment, the resonant chamber 2 is a separate chamber isolated from the other chambers 3, with walls surrounding the chamber, and only one wall of the chamber includes at least one opening configured to be in communication with the other chambers 3. The material forming the walls of the resonant chamber 2 includes rigid materials and includes the same type of material. The walls of the resonant chamber include materials such as polypropylene (PP), polycarbonate (PC), poly (ethylene terephthalate)-1,4-cyclohexanedimethanol ester (PCTG), polyamide (PA), or polyetheretherketone (PEEK). In some implementations, the walls of the resonant chamber 2 may also incorporate other materials like silicone or metal. The resonant chamber 2 is at least partially integrally formed with the casing 4 (at least a part of the resonant cavity 2 shares the same wall with at least a part of the casing 4), or it may be connected using physical connectors like snap-fittings or hooks, or through chemical connectors such as adhesives. Furthermore, the resonant chamber 2 is provided on the edge portion of the casing 4 of the noise-reducing gas passage device 1, close to the external environment, which is structurally more favorable for manufacturing and assembly than resonant chambers provided within other chambers 3. Additionally, the at least one resonant chamber 2 has a volume that is less than or equal to the combined volume of the other chambers 3. Since the resonant chamber 2 has a smaller volume than the other chambers 3, it is possible to establish a vertical height difference between at least one of the centers of the first chamber 31 and the second chamber 32 and the center of the resonant chamber 2. This height difference can be due to the vertical alignment of the resonant chamber 2 with the other chambers 3 or because the resonant chamber 2 is parallel to other chambers 3 but shorter in height. In one implementation where the resonant chamber 2 and the other chambers 3 are vertically aligned within the noise-reducing gas passage device 1, and both the resonant chamber 2 and the first chamber 31 housing the blower 5 are positioned near the exterior of the casing 4, the chambers are arranged from top to bottom as follows: the first layer is the first chamber 31, the second layer is the second chamber 32, and the third layer is the resonant chamber 2. In this arrangement, the distance between the center point of the resonant chamber 2 and the center point of the first chamber 31 is greater than the distance between the center point of the first chamber 31 and the center point of the second chamber 32 (as depicted in FIG. 4, where d1 represents the height of the first chamber 31, d2 represents the height of the second chamber 32, and d3 represents the height of the resonant chamber 2). Moreover, the communication between the resonant chamber 2 and the other chambers 3 is formed through a neck 21, which includes a first end part 211 connected to the opening of the resonant chamber 2 and a second end part 212 connected to other chambers 3. The first end part 211 and the second end part 212 are interconnected through openings in the walls of the resonant chamber 2 and the other chambers 3. The neck 21 is typically a straight, unbent conduit that spans a certain length (as shown in FIG. 6, where the height of the neck is d4), and cross-sections of the neck 21 are the same at the same angle from the first end part 211 to the second end part 212. The cross-section of the neck 21, corresponding to the inner wall's normal cross-section of the neck 21 (i.e., cross-sections of the neck at the same angle are of a uniform shape, typically being circular or elliptical). However, other shapes such as square, diamond, or any other configurations for the cross-section of the neck 21 are also permissible (as shown in FIG. 5). The cross-sectional area of the neck is at least 0.19625 $mm^2$, and the structure of the neck 21 is primarily configured to connect chambers without substantial or any airflow passing through it (i.e., the airflow entering the neck 21 is at most 20% of the airflow entering the air intake 41 of the casing 4). Consequently, the orientation of the central line of the neck 21 is restricted, and the airflow in the other chambers 3 forms a main airflow path (the main flow path for the majority of the airflow within the chamber). The angle between the tangent at the second end part 212 of the main airflow path and the central line of the neck 21 is set to be at least 30° (as shown in FIG. 7, where za1 and za2 represent two different inclinations of the neck 21, with both angles being at least) 30°. In one implementation, the noise-reducing gas passage device 1 includes a blower 5 provided within the other chambers 3 that pressurizes the air, with the axis of the blower 5 parallel to the central line of the neck 21. This configuration is applicable when the blower 5 is provided inside the chamber such that its axis is perpendicular to the horizontal plane, and the neck 21 is an unbent vertical channel. In some types of gas passages, where noise control is managed adequately, the noise-reducing structure of noise-reducing gas passage device 1 is configured to perform noise reduction solely through the resonant chamber 2. In some implementations, the other chambers 3 house a noise-reducing component that works in conjunction with the resonant chamber 2 to reduce noise. This approach further reduces noise, such as in the other chambers 3 of the noise-reducing gas passage device 1, which have multiple walls of the same form spaced at a certain distance apart, configured to perform noise reduction processing on the airflow entering the chamber. A certain distance here can be understood as either the same or a different distance, with this distance being greater than or equal to 0.8 mm.

The noise reduction principle of the noise-reducing gas passage device 1 with the resonant chamber 2 involves providing a closed chamber (the resonant chamber 2) in communication with a narrow passage (the neck 21), configured as an acoustic filter using principles of resonance and negative pressure to reduce noise at specific frequencies. The process is as follows: gas enters the noise-reducing gas passage device 1 through the air intake 41 on the casing 4 and flows in a predetermined direction along a pre-set airflow path. This path is the main airflow path within the noise-reducing gas passage device 1, guiding the majority of the airflow. The structure of the resonant chamber 2 and the neck 21 ensures that, when the device 1 is operational, gas flows within the other chambers 3 and hardly enters the resonant chamber 2. Here, "hardly" is specifically defined as the ratio of the airflow entering the resonant chamber 2 to the total airflow within the device 1 being less than or equal to 0.2. As the airflow passes through the second end part 212 of the neck 21, periodic negative pressure is generated within the resonant chamber 2 (when negative pressure forms, the air volume inside the resonant chamber 2 decreases, reducing the medium for sound propagation within the chamber 2 and thus blocking the transmission of sound, which is one aspect of noise reduction). Sound waves enter the resonant chamber 2 through the neck 21, causing air within the chamber to resonate. During this resonance, a large amount of sound energy is absorbed and converted into heat energy, thereby reducing the sound intensity and achieving noise reduction. More specifically, as the airflow passes through the second end part 212 of the neck 21 in the noise-reducing gas passage device 1, sound waves incident on the neck 21 cause the air within the neck to vibrate. Due to the elongated structure of the neck 21, this vibration creates an "air piston effect" (similar to the reciprocating motion of a piston in a cylinder), continuously transmitting the sound wave energy into the resonant chamber 2. Within the resonant chamber 2, sound waves undergo alternating compressive and rarefactive movements, forming standing waves (during the compressive phase, the air column in the neck 21 pushes air into the resonant chamber 2, increasing the pressure within; during the rarefactive phase, the air column pulls back, allowing air to flow out of the resonant chamber 2, decreasing the pressure within). However, due to the air's viscous resistance and friction with the chamber walls, the vibrations within the resonant chamber 2 dissipate the sound wave energy into heat through viscous dissipation and thermal conduction, significantly reducing the energy of the transmitted sound waves and thus achieving sound attenuation. The dimensions, shapes, and material properties of the neck 21 and the resonant chamber 2 significantly influence the flow of air and sound waves, as well as the noise reduction effectiveness.

The principle is based on the formula for Transmission Loss (TL) which is given by:

$$TL = 20 \cdot \log_{10}\left(\frac{1}{1 + \frac{Z_{neck}}{Z_{pipe}} \cdot e^{-2jkx}}\right)$$

Here, TL is the transmission loss (in decibels, dB), $Z_{neck}$ is the acoustic impedance of the neck 21, and $Z_{pipe}$ is the acoustic impedance of the main pipe. J represents the imaginary unit, k is the wave number, and X is a parameter related to dimensions. The acoustic impedance of the neck 21 can be calculated as:

$$Z_{neck} = \rho c\left(\frac{A_{neck}}{A_{pipe}}\right)$$

where ρ is the density of air, c is the speed of sound in air, $A_{neck}$ is the cross-sectional area of the neck 21, and $A_{pipe}$ is the cross-sectional area of the main pipe, which corresponds to the cross-sectional area of the passage where the main airflow passes through the second end part 212 of the neck 21.

X can be derived from the following expression:

$$x = \frac{2\pi}{c}\sqrt{\frac{A_{neck}}{A_{pipe} \cdot V}}$$

where V is the volume of the resonant chamber 2. K can also be calculated using the expression:

$$k = \frac{Z_{neck}}{Z_{pipe}} \cdot \sqrt{\frac{A_{neck}}{A_{pipe}}}$$

where $Z_{neck}$ is the acoustic impedance of the neck 21 and $Z_{pipe}$ is the acoustic impedance of the main pipe. The resonance frequency fres can be calculated from the following formula:

$$fres = \frac{c}{2\pi}\sqrt{\frac{S}{Vl}}$$

where c is the speed of sound in air, S is the area of the opening of the neck 21, V is the volume of the resonant chamber 2, and I is the length of the neck 21. From the above formula, it is understood that the greater the Transmission Loss (TL), the better the noise reduction effect of the resonant chamber 2, and that parameters affecting the noise reduction include the volume V of the resonant chamber 2 and the area of the neck 21, $A_{neck}$. Based on adjustments to the parameters mentioned above, calculations and experiments were conducted to determine the optimal chamber structure for the noise-reducing gas passage device 1. By adjusting these parameters and conducting experiments, the optimal chamber structure for the noise-reducing gas passage device 1 is determined, resulting in the best version of the noise-reducing gas passage device 1 for noise reduction. The disclosure discussed herein identifies the following parameters for a structure of the noise-reducing gas passage device 1 with effective noise reduction: the ratio of the height of the neck 21 to the height of the resonant chamber 2 is at least 1:300. When the cross-section of the neck 21 is circular or elliptical, the diameter of the circle or the major axis of the ellipse is at least 0.5 mm, and the volume of the resonant chamber 2 is at least 785 $mm^3$.

Figure 8:
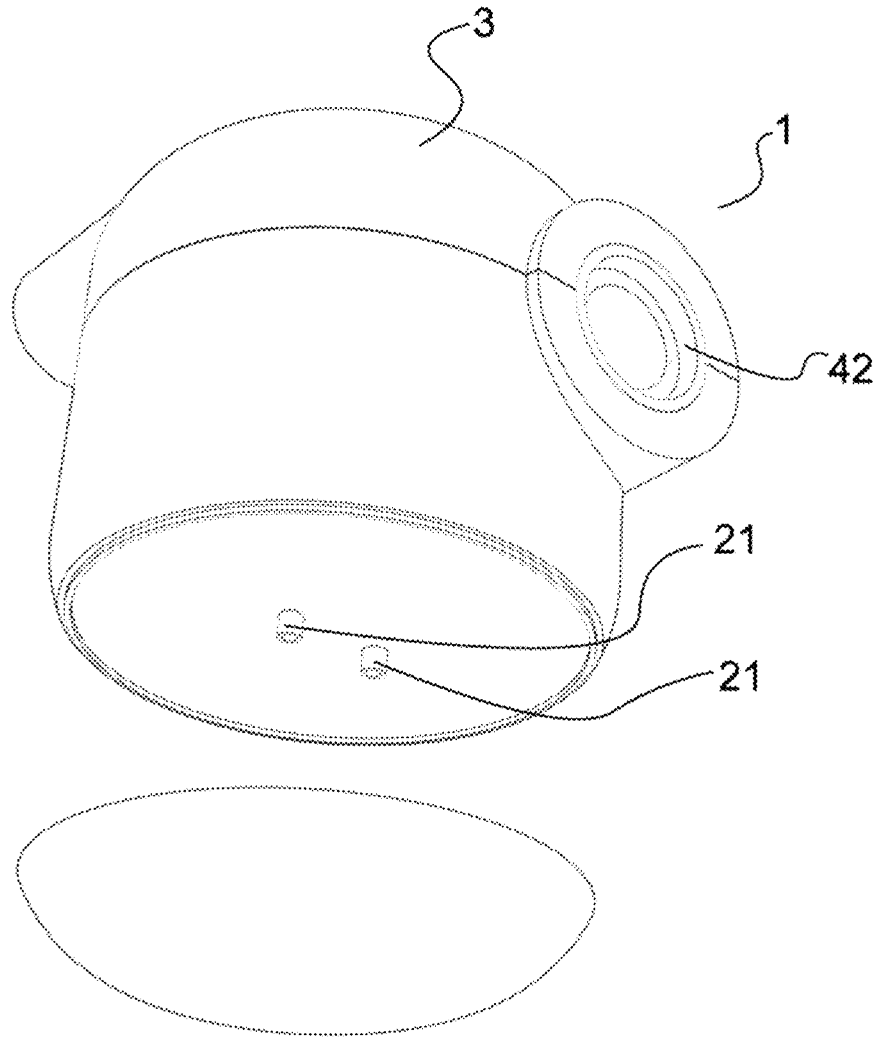
FIG. 8 shows a schematic diagram showing a noise-reducing gas passage device with a resonant chamber that includes multiple necks in one of the walls of the resonant chamber in accordance with one embodiment.

In one implementation, the noise-reducing gas passage device 1 has multiple necks 21 to communicate the resonant chamber 2 with the other chambers 3, where the resonant chamber is formed by walls surrounding the resonant chamber, and only one of the walls of the resonant chamber has multiple necks 21 or openings (as shown in FIG. 8)

Figure 9:
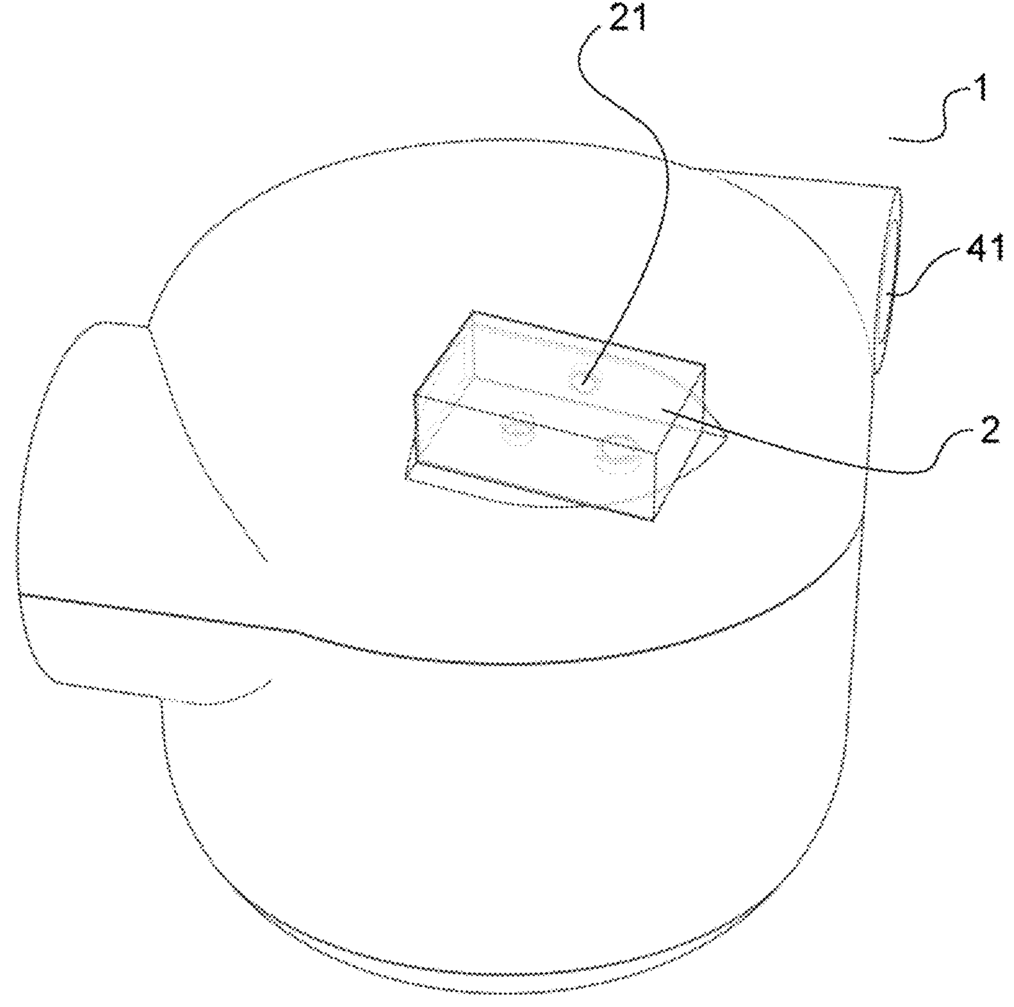
FIG. 9 shows a schematic diagram of a noise-reducing gas passage device with necks in multiple walls of the resonant chamber, from another embodiment in accordance with one embodiment.

In one implementation, the noise-reducing gas passage device 1 includes multiple necks 21 to communicate the resonant chamber 2 with the other chambers 3, where one configuration includes multiple walls of the resonant chamber 2 having necks 21 or openings (as shown in FIG. 9).

Figure 10:
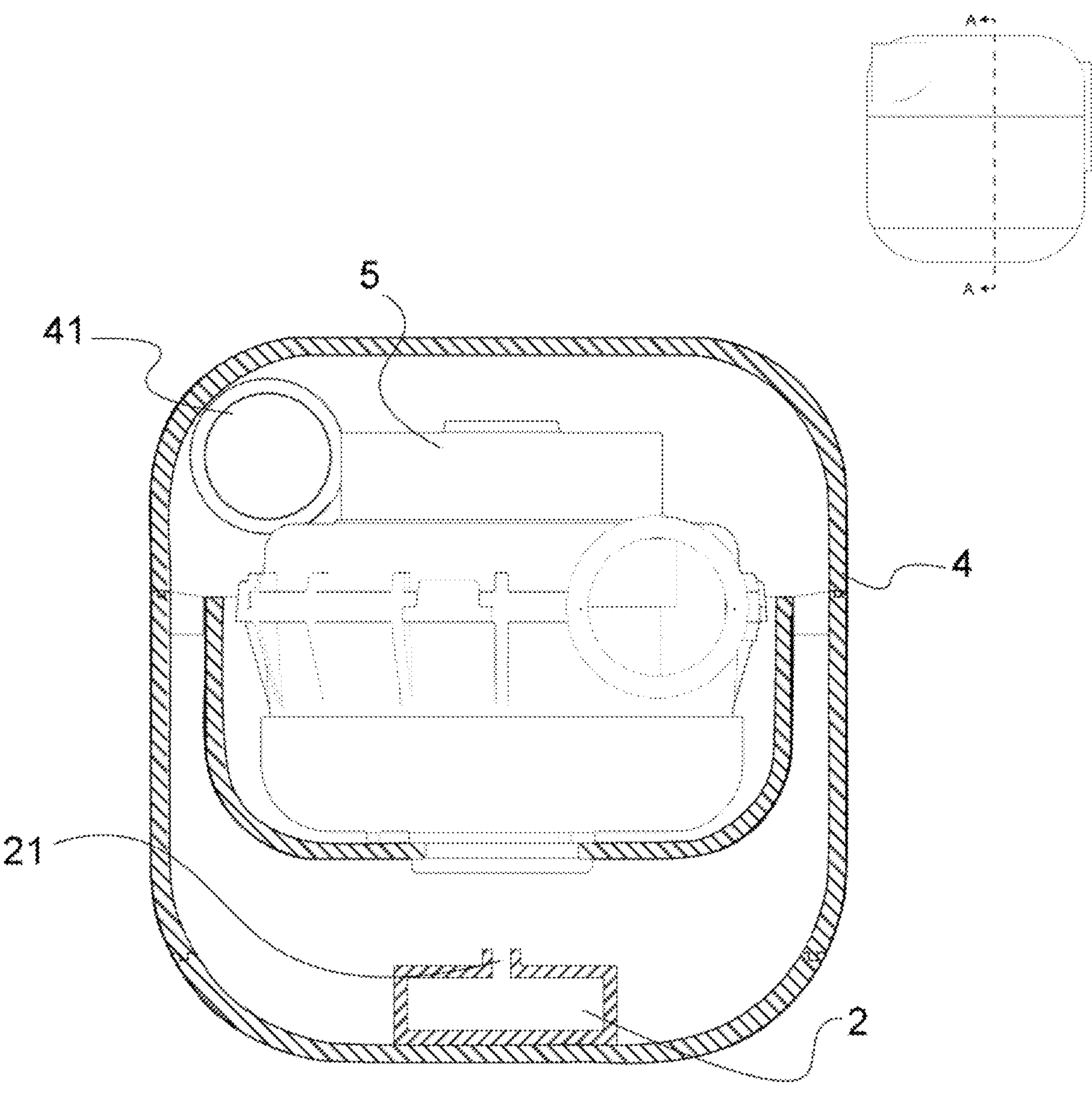
FIG. 10 shows the noise-reducing gas passage being provided within other chambers in accordance with one embodiment.

In another implementation, the resonant chamber 2 is provided inside at least one of the other chambers 3, meaning that other chambers 3 enclose the resonant chamber 2 (as shown in FIG. 10).

Figure 11:
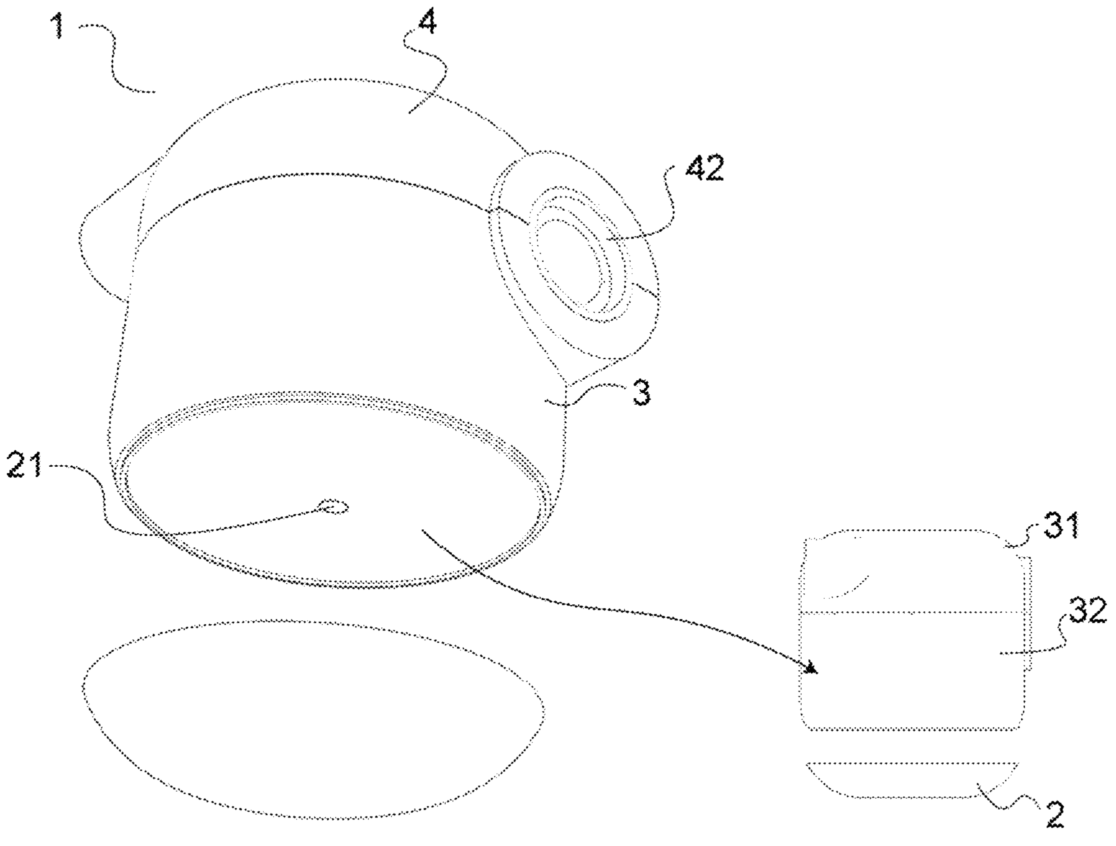
FIG. 11 shows a schematic diagram of the neck within the gas passage, which is an opening without height in accordance with one embodiment.

In yet another implementation, the neck 21 is formed by the wall thickness at the connection point between the other chambers 3 and the resonant chamber 2, meaning the height of the neck 21 is the sum of the wall thicknesses at this point between the other chambers 3 and the resonant chamber 2 (as shown in FIG. 11).

Embodiment 2

Figures 12A, 12B, 12C:
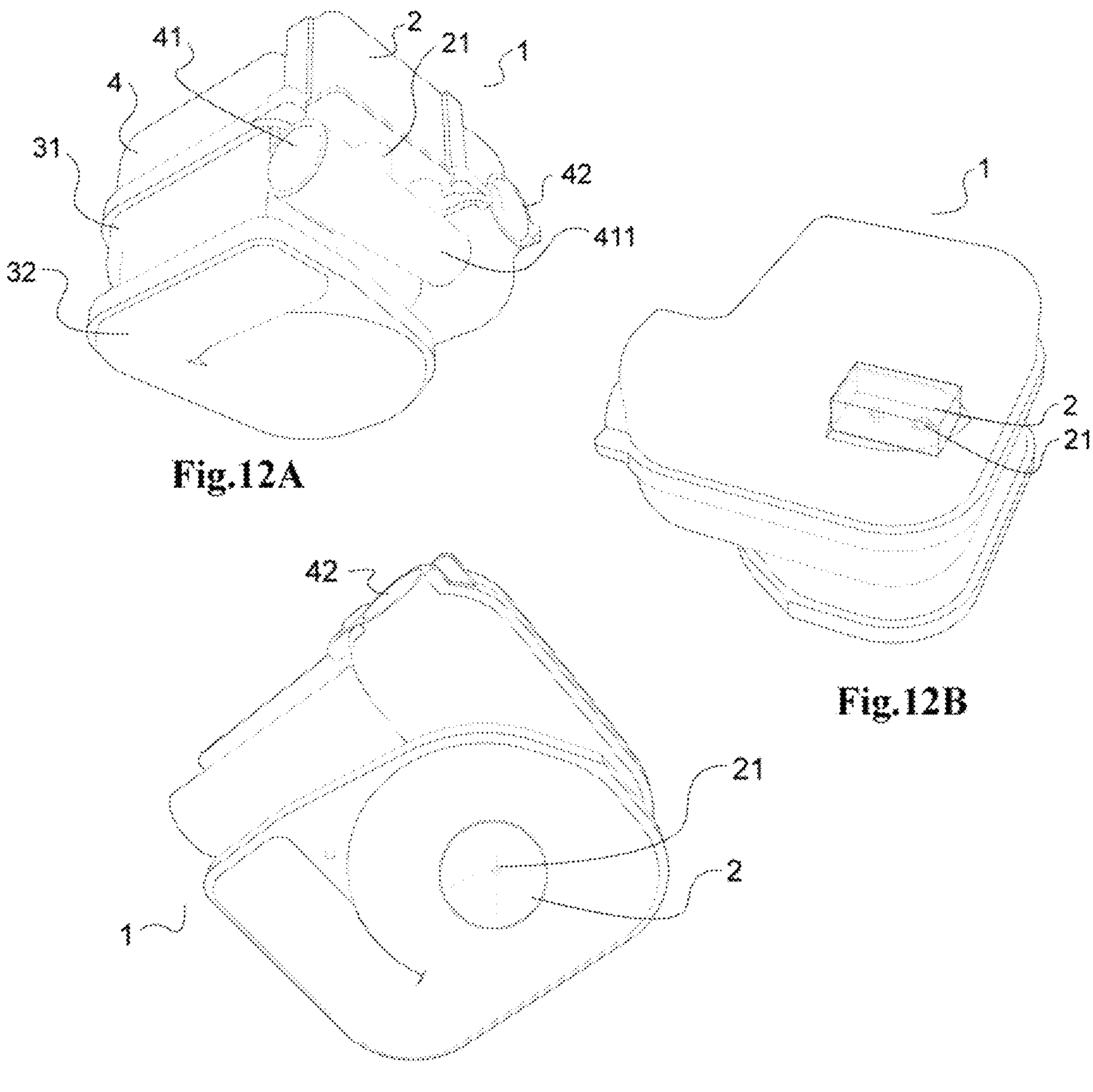
FIGS. 12A, 12B, and 12C show schematic diagrams of a noise-reducing gas passage device with a resonant chamber connected to the intake pipe, first chamber, and second chamber in accordance with one embodiment.
Figure 13:
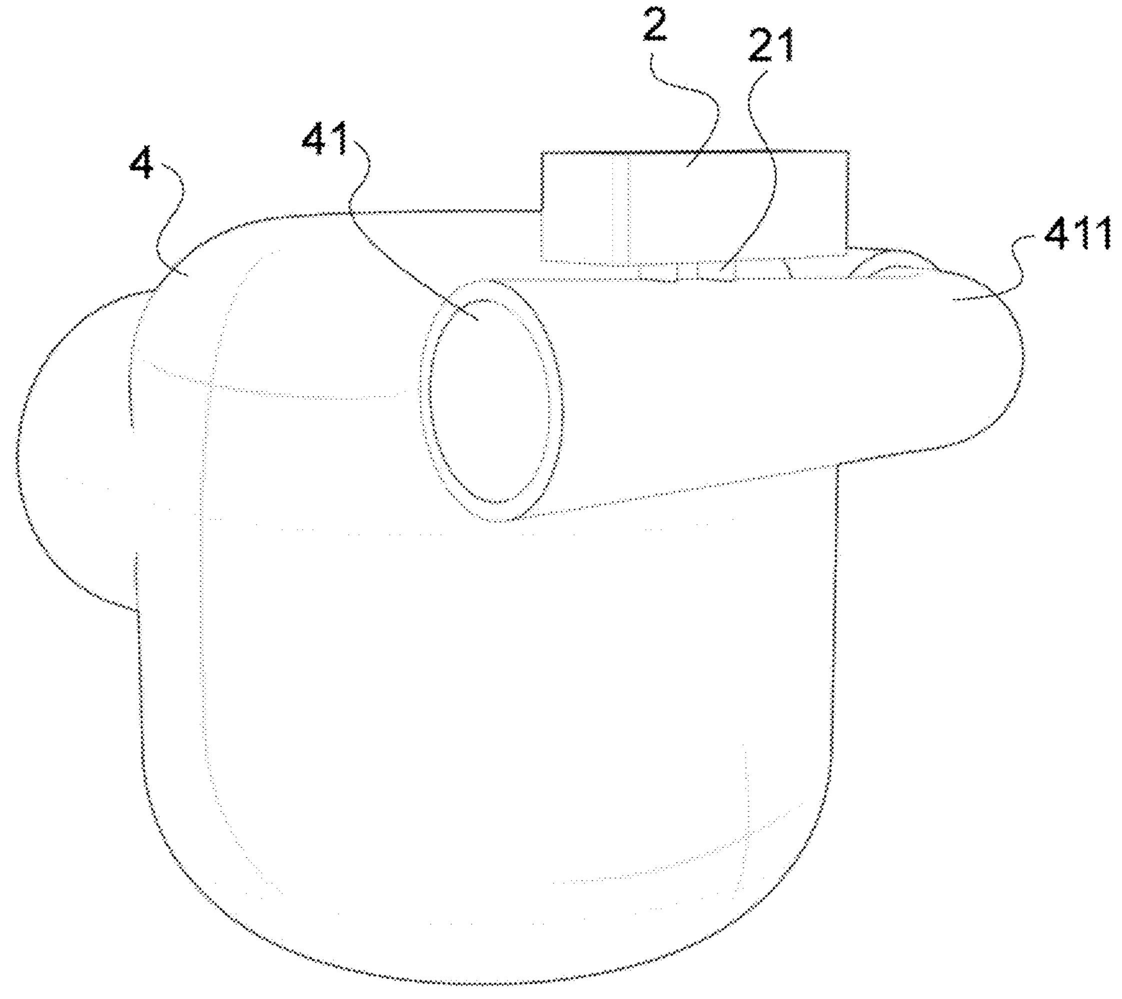
FIG. 13 shows a schematic diagram of a noise-reducing gas passage device with an intake pipe connected to the resonant chamber in accordance with one embodiment.

This embodiment introduces a noise-reducing gas passage device 1 with a resonant chamber 2, as shown in FIGS. 12A, 12B, and 12C. This embodiment provides a three-dimensional schematic diagram of the structure of the noise-reducing gas passage device 1. A notable difference from Embodiment 1 in this embodiment, as illustrated in FIGS. 12A, 12B, and 12C, is the positioning of the resonant chamber 2. In this disclosure, the resonant chamber 2 serves as the core component of the noise-reducing structure and is highly flexible and adaptable. It can be integrated with variously structured chambers to construct different configurations of the noise-reducing gas passage device 1. In some cases, the structure of the noise-reducing gas passage device 1 may differ from that in Embodiment 1. The positioning of the resonant chamber 2 relative to the blower 5 and the other chambers 3 also has various possibilities. In one implementation, the axis of the blower 5 is parallel to the central line of the neck 21, as depicted in FIGS. 12A, 12B, and 12C. Here, FIG. 12A indicates that the resonant chamber is in communication with the intake pipe of the noise-reducing gas passage device 1 in this embodiment, FIG. 12B shows the resonant chamber 2 communicating with the first chamber of the noise-reducing gas passage device 1 in this embodiment, and FIG. 12C indicates communication of the resonant chamber 2 with the second chamber of the noise-reducing gas passage device 1 in this embodiment. In addition, in this embodiment, the structure of the resonant chamber 2 is modularized, configured as a simple cubic structure that serves as a basic volume block. This shape of the resonant chamber 2 facilitates its integration as an additional, independent, and complete simple module with any other shape of the noise-reducing gas passage device 1. It retains the same structural features and functional effects as in Embodiment 1, whether it's noise reduction effectiveness, negative pressure effects, or airflow characteristics. This simple cubic structure of the resonant chamber 2 ensures that the excellent performance consistent with the original design is maintained, and simultaneously enhances the scalability of the noise-reducing gas passage device 1. It is worth noting that when the resonant chamber 2 is connected to the intake pipe 411, it offers a greater advantage in terms of noise reduction compared to placing the resonant chamber 2 in other positions. The cross-section area of the channel of the intake pipe 411 is smaller compared to the cross-section areas of the channels within the other chambers, which facilitates a more concentrated and stable flow of air within the intake pipe 411, consequently generating higher airflow pressure and velocity. The cross-sectional area of the intake pipe 411 is smaller compared to the channels within the chambers, which promotes more concentrated and stable airflow within the intake pipe 411, thereby generating higher airflow pressure and velocity. Furthermore, because of the positional relationship between the intake pipe 411 and the resonant chamber 2, the direction of the airflow moving within the intake pipe 411 is more uniform, and the likelihood of turbulent airflow is reduced. Consequently, less airflow enters the resonant chamber 2, which is advantageous for noise reduction using the principle of negative pressure. The difference in flow velocity and pressure between the intake pipe 411 and the resonant chamber 2 creates a negative pressure area at the second end part 212 of the neck 21. When the resonant chamber 2 is connected to this negative pressure area, the airflow passing through the second end part 212 of the neck 21 reacts more quickly with the resonant chamber 2 to reduce noise and further enhances the negative pressure effect during this reaction. Since the internal medium is sparse, this limits the propagation of sound, therefore, less sound is transmitted outside the resonant chamber 2. This structural arrangement enhances the performance effectiveness and reliability of this design in the noise-reducing gas passage device 1. This reinforced negative pressure effect not only effectively reduces noise within the airflow but also provides a quieter and more comfortable treatment environment for patients while maintaining stable airflow volume and pressure in the ventilator.

Embodiment 3

Figure 14:
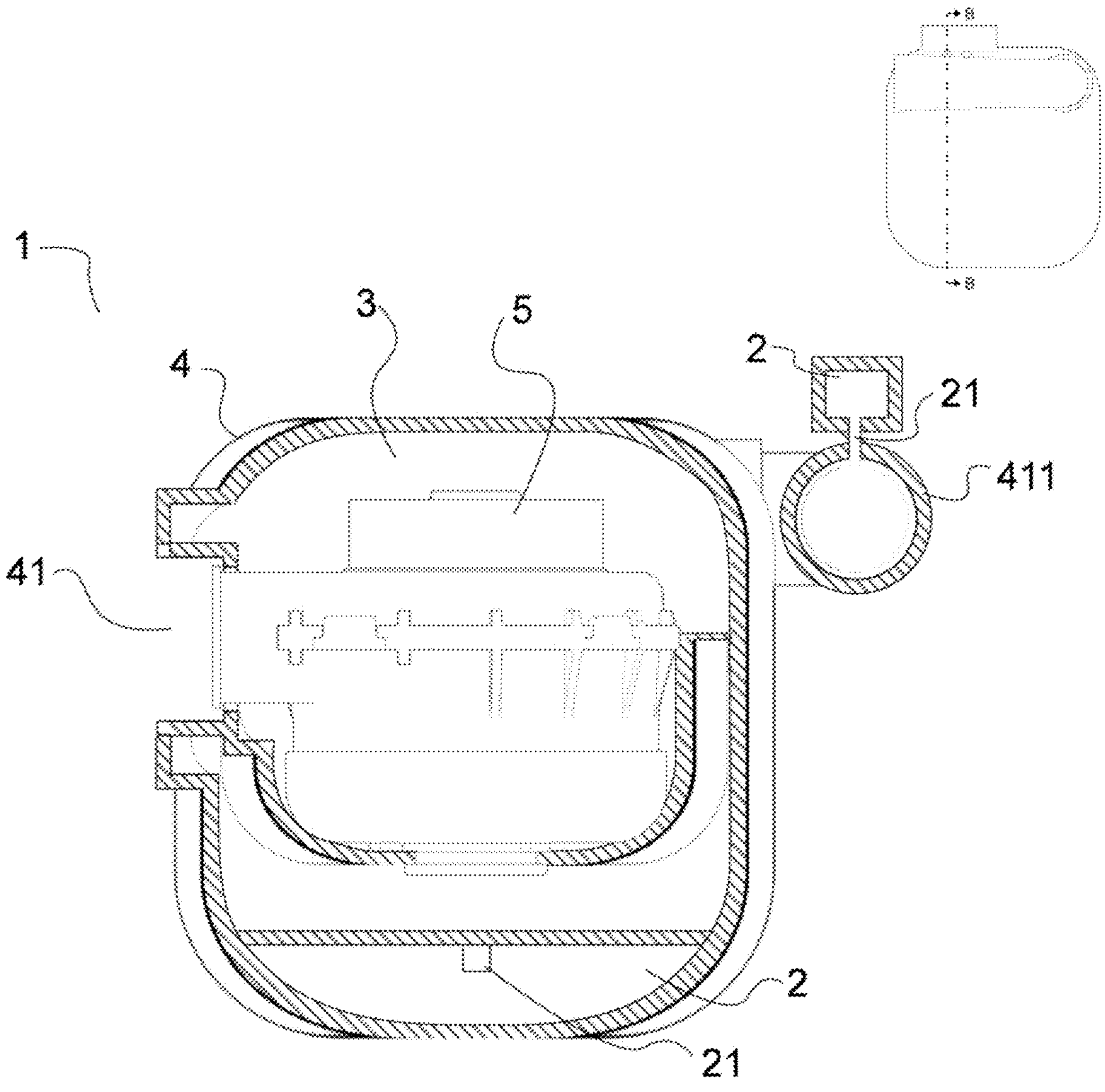
FIG. 14 shows a schematic diagram of a noise-reducing gas passage device with multiple resonant chambers in accordance with one embodiment.
Figure 15:
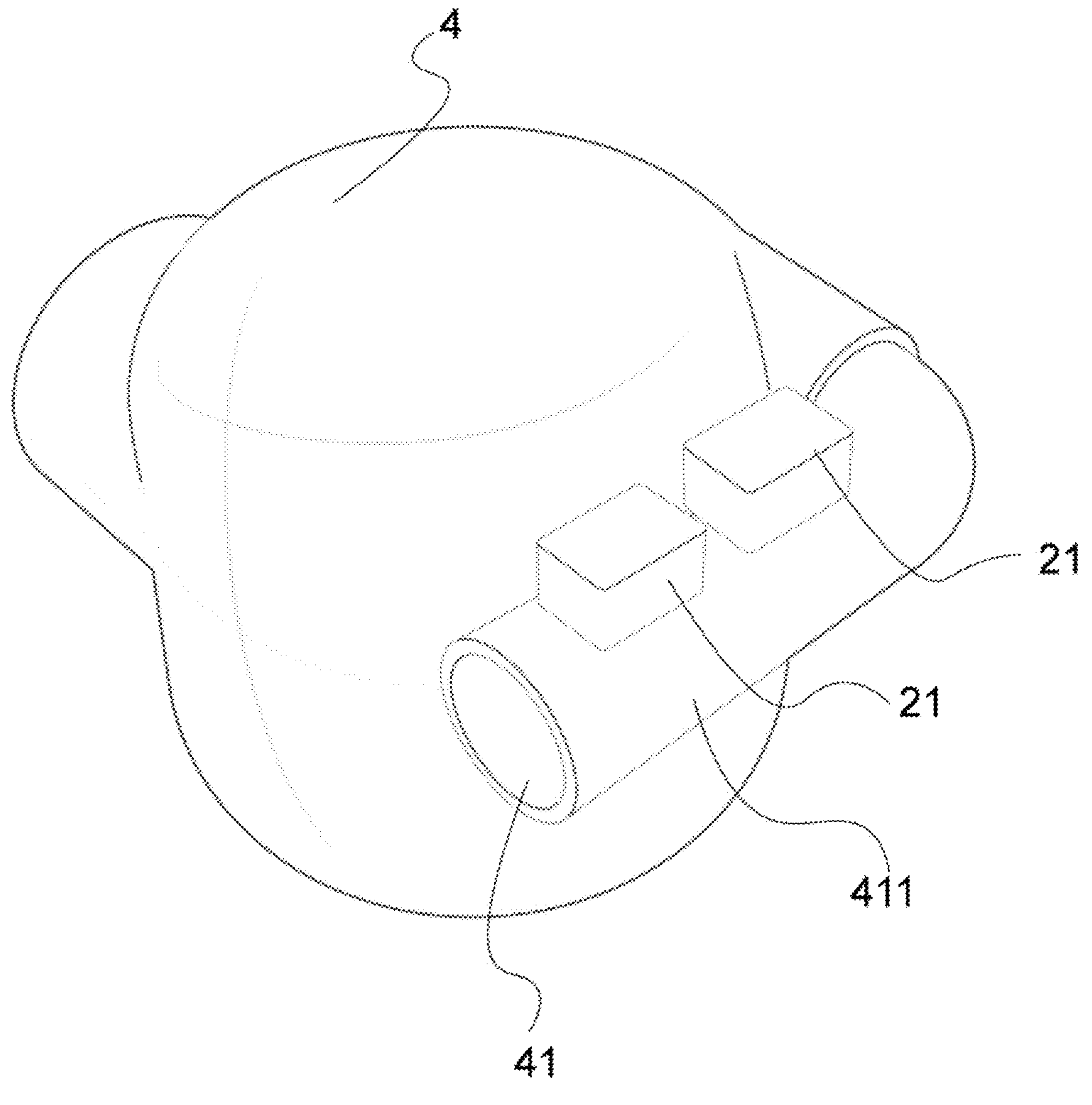
FIG. 15 shows another schematic diagram of a noise-reducing gas passage device with multiple resonant chambers in accordance with one embodiment.

This embodiment introduces a noise-reducing gas passage device 1 configured with multiple resonant chambers 2, as depicted in FIGS. 14 and 15. This embodiment provides a three-dimensional schematic diagram of the structure of the noise-reducing gas passage device 1. In the implementations shown in FIGS. 14 and 15, unlike in Embodiment 1, the noise-reducing gas passage device 1 includes more than one resonant chamber 2. Multiple resonant chambers 2 within the noise-reducing gas passage device 1 can be arranged in various forms, such as multiple resonant chambers 2 at the same location of the noise-reducing gas passage device 1 being arranged in a specific manner (as shown in FIG. 15, where the noise-reducing device 1 includes two parallel resonant chambers 2 connected to the intake pipe 411). This layout at the same location can more thoroughly dissipate sound waves, offering particular advantages in areas with high noise levels. The arrangement of multiple resonant chambers 2 in such locations can enhance noise reduction effectiveness significantly. In another implementation, the noise-reducing gas passage device 1 has multiple resonant chambers 2 provided at different locations, each configured to reduce noise in the airflow of the other chambers 3 (as shown in FIG. 14, where two resonant chambers 2 are in communication with the intake pipe 411 and with a second chamber 32 that does not house the blower 5). This design allows each resonant chamber 2 to target different noise sources, achieving more comprehensive noise control in the gas passage device 1. In a specific implementation, when a resonant chamber 2 is in communication with the second chamber 32 connected to the blower 5's inlet, and the second end part 212 of the neck 21 directly faces the blower 5's inlet, a particularly effective negative pressure mechanism is formed. When the blower 5 operates, intense suction at the blower 5's inlet causes air inside the resonant chamber 2 directly in communication with it to be rapidly drawn in, creating a localized negative pressure environment. This negative pressure mechanism not only enhances the resonance effects of the sound waves within the resonant chamber 2 but also further optimizes the airflow, improving the stability and uniformity of the airflow.

Embodiment 4

Figure 16:
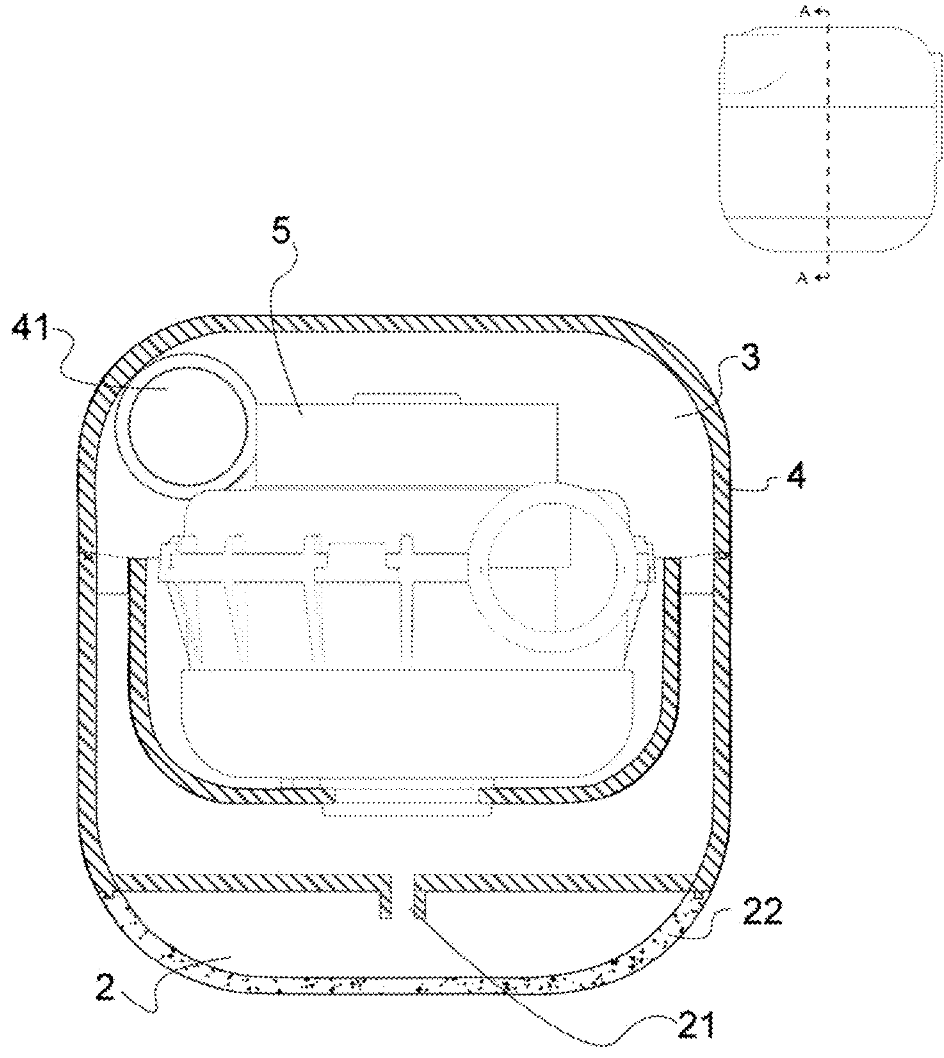
FIG. 16 shows a schematic diagram of a noise-reducing gas passage device in which the resonant chamber includes two different materials in accordance with one embodiment.

This embodiment introduces another noise-reducing gas passage device 1 configured with a resonant chamber 2, as illustrated in FIG. 16. This embodiment provides a three-dimensional schematic diagram of the noise-reducing gas passage device 1. In the embodiment shown in FIG. 16, unlike the noise-reducing gas passage device in Embodiment 1, the walls of the resonant chamber 2 include at least two different materials. In one implementation, the walls of the resonant chamber 2 include a rigid material identical to that of the casing 4, which forms the base structure of the resonant chamber, ensuring its stability and durability. Simultaneously, a second material 22, different from the rigid material and possessing superior sound absorption or insulation properties, complements the inherent noise reduction capabilities to further enhance the noise attenuation. The second material 22 could be foam, silicone, a metal material, or any other suitable material. This approach leverages the distinct properties and acoustic roles of different materials to achieve better noise reduction. In implementations where the walls of the resonant chamber 2 incorporate foam material, given that foam is an effective sound-absorbing material, sound waves entering the resonant chamber 2 undergo energy transformation within the foam's porous structure. This mechanism ensures maximum energy loss of sound waves within the resonant chamber 2, resulting in more thorough noise reduction. Moreover, the design of the resonant chamber 2 using multiple materials not only enhances the noise reduction level of the noise-reducing gas passage device 1 to some extent but also offers greater flexibility for future optimization and modification of the device. This allows adjustments based on specific application needs and acoustic performance, enabling more effective noise reduction within certain frequency ranges.

Implementing the noise-reducing gas passage device 1 with a resonant chamber as described in this disclosure provides several beneficial effects:

1. The integration of the resonant chamber with the noise-reducing gas passage device offers an innovative noise reduction structure to the ventilator market that is highly efficient and reliable. The design of the resonant chamber is inspired by muffler technology, which is supported by reliable computational models. Experimental validation of this disclosure has confirmed that this resonant chamber structure is suitable for use in ventilators and noise-reducing gas passage devices in other related machines, where it can significantly reduce noise levels. The technology, based on the principles of sound wave resonance and negative pressure, efficiently dissipates and absorbs sound waves at specific frequencies. This noise-canceling mechanism is particularly crucial in the presence of high-noise sources such as blowers within the noise-reducing gas passage devices. This disclosure not only applies traditional noise cancellation technology to ventilators but also thoroughly considers the airflow dynamics and acoustic characteristics within respiratory machines, integrating them closely with the noise-reducing gas passage devices. Through in-depth research and precise design and adjustment of the resonant chamber and neck parameters, a superior noise reduction effect can be achieved, providing patients with a quieter and more comfortable usage environment. As patients' demand for high-quality, low-noise respiratory products continues to grow, respiratory products employing this noise reduction technology can meet market needs effectively.
2. This Disclosure Introduces a Resonant Chamber as a New and Simple Noise reduction structure that not only effectively reduces noise but also offers several advantages over traditional foam used within chambers of noise-reducing gas passage devices. These advantages include: (1) In 2021, a prominent international brand issued its first global recall affecting some of its Bi-level Positive Airway Pressure (BiPAP) devices, Continuous Positive Airway Pressure (CPAP) devices, and mechanical ventilators, and subsequent recalls were also issued, primarily due to the noise-reducing foam used inside the noise-reducing gas passage devices. The U.S. Food and Drug Administration (FDA) requires ventilators to achieve a noise level below 30 dB to receive marketing approval. Currently, using foam for noise reduction is the simplest method because foam materials are readily available and easy to manufacture. Foam's unique porous structure and material properties enable it to convert noise into minimal energy, effectively achieving significant noise reduction. Placing foam within the noise-reducing gas passage device is a common, simple, and effective way to meet these regulatory noise level requirements. This method is widely used due to its straightforward implementation that allows for effective sound absorption. However, foam has several potential disadvantages related to human health and can pose environmental hazards. These include: a. Foam is typically made from synthetic materials that may contain chemical additives. These chemicals can leach out as the foam ages and degrades, potentially increasing the health risks to patients over time. In contrast, the innovative noise-reducing structure proposed by this disclosure, which can be integrally formed with the casing of the noise-reducing gas passage device, does not pose the same hazards associated with foam. b. Due to its soft and relatively loose surface, foam can be worn away or peeled off by airflow, releasing particles. These particles can enter the patient's respiratory tract with the airflow, potentially causing irritation and respiratory issues such as throat pain and coughing, particularly in individuals with pre-existing conditions like asthma or Chronic Obstructive Pulmonary Disease (COPD). c. Foam can accumulate dust, bacteria, and other contaminants over time. Particularly in respiratory machines, foam is not easily washable and moisture from breath can promote bacterial growth and infection risks. To prevent these issues, particularly in the design of respiratory-related machines, it is crucial to avoid using materials that can generate particulate matter. d. Due to the components of foam, the production and recycling processes of foam generate certain harmful gases. The resonant chamber structure in the noise-reducing gas passage device offers efficient noise reduction capabilities, which means that the use of foam materials can be reduced in these devices, thereby decreasing the respiratory machine market's reliance on and use of foam materials. This alternative approach not only meets the urgent needs of modern society for environmental protection and sustainable development but also aligns with the overall goals of green development. (2) Using the effective noise-reduction structure of this disclosure instead of foam can extend the lifespan of respiratory-related machines. Foam is typically made from synthetic materials like polyurethane and polyether, which are more susceptible to environmental influences, resulting in a shorter lifespan compared to materials like plastic or silicone. In contrast, devices with a resonant chamber for noise-reducing gas passage device achieve regulatory noise levels without the extensive use of foam within the chamber, enhancing the device's durability. Additionally, noise-reducing gas passage devices without internal foam do not require complex structures to secure foam, simplifying the internal structure and reducing complexity, which helps to further improve the reliability and stability of the device. (3) As the market for respiratory-related machines grows, more patients have varying preferences and needs. Some patients prioritize health and safety and may opt for noise-reducing gas passage devices that do not contain internal foam, while others who have higher noise sensitivity may prefer devices that ensure a quieter environment. Therefore, considering individual needs and preferences, and under the premise of ensuring safety, soundproofing materials (including silicone, gel, and small amounts of foam that can isolate or absorb noise) may be added to the chambers of noise-reducing gas passage devices to achieve lower noise levels. Soundproofing materials include foam, silicone, and other soft materials. Adding foam within the chambers of devices with a resonant chamber can further reduce noise and offer more options to patients. This flexible design approach provides a more personalized and considerate respiratory treatment experience, further enhancing patients' sleep quality and life quality.

3. The structure is simple and cost-effective, making it a more economical choice. The requirements for the resonant chamber are merely a chamber surrounded by walls, with at least one wall including at least one neck (or opening). This structure is simpler and more straightforward compared to the noise reduction structures in noise-reducing gas passage devices currently available on the market. The simplicity of the resonant chamber's design not only makes it more streamlined but also easier to manufacture and assemble. This means that noise-reducing gas passage devices with a resonant chamber are easier to produce than existing noise-reducing structures in noise-reducing gas passage devices, with reduced process and material costs during manufacturing. Therefore, although this design increases the difficulty of initial design and research, and the cost of research and development through dozens of model validations, it can effectively reduce manufacturing costs in the later stages, providing patients with an economical and efficient noise reduction solution. Additionally, a simpler structure not only means lower manufacturing costs but also enhances production efficiency, potentially shortening production cycles and further reducing overall production costs, helping to achieve widespread application in the market.
4. Highly adaptable, easy to integrate, and does not affect airflow. Due to their simple structure, the resonant chamber and neck can be easily and conveniently integrated into the structure of existing noise-reducing gas passage devices without the need for significant modifications to the existing designs, allowing minimal changes to the resonant chamber itself. This offers manufacturers greater freedom in production and design. Additionally, by adjusting parameters of the neck and the resonant chamber such as the cross-sectional area of the neck and the volume of the resonant chamber, it is possible to tailor the noise reduction more precisely for specific sound-emitting components according to their sound frequencies and requirements, fulfilling the need for customized noise reduction in different noise-reducing gas passage devices. Furthermore, since the resonant chamber essentially acts as a true cavity that with no airflow entering, primarily interacting with sound waves rather than the airflow, it influences sound waves without affecting the airflow. This means it does not impact the flow rate and pressure of the main function of the noise-reducing gas passage devices (i.e., providing airflow of specific volume and pressure). Therefore, the airflow can maintain its original specified volume and pressure when passing through the noise-reducing gas passage device with a resonant chamber. Overall, the resonant chamber structure introduced by this disclosure provides the market for respiratory-related machines with a flexible, efficient, and reliable noise reduction solution.

It must be noted that as used herein and in the appended claims, the regular forms "a" "an" "the" include their plural equivalents, unless the context clearly dictates otherwise.

The invention claimed is:

1. A noise-reducing gas passage device comprising a resonant chamber, configured to generate pressurized gas and continuously deliver it to a patient's respiratory tract, the noise-reducing gas passage device comprising:

a casing, configured to include at least two chambers comprising at least one resonant chamber, an air intake, and an air outlet, wherein the air intake is configured to receive gas and the air outlet is configured to exhaust the pressurized gas; and the at least one resonant chamber is empty, including walls surrounding the at least one resonant chamber, wherein at least one wall of the at least one resonant chamber includes at least one opening configured to be in communication with other chambers of the at least two chambers other than the at least one resonant chamber;

wherein, when the noise-reducing gas passage device is operational, the gas flows in the at least two chambers other than the at least one resonant chamber without substantially entering the at least one resonant chamber;

wherein, a volume of the at least one resonant chamber is less than or equal to a combined volume of the at least two chambers other than the at least one resonant chamber;

wherein, from top to bottom, the noise-reducing gas passage device sequentially comprises a first chamber of the at least two chambers and a second chamber of the at least two chambers, and wherein the first chamber is configured to accommodate a blower.

2. The noise-reducing gas passage device according to claim 1, wherein the at least one resonant chamber is provided at an edge portion of the casing of the noise-reducing gas passage device.

3. The noise-reducing gas passage device according to claim 1, wherein a height difference is provided between a central point of at least one of the first chamber and the second chamber and a central point of the at least one resonant chamber.

4. The noise-reducing gas passage device according to claim 3, wherein a distance between the central point of the at least one resonant chamber and the central point of the first chamber is greater than a distance between the central point of the first chamber and the central point of the second chamber.

5. The noise-reducing gas passage device according to claim 1, wherein the at least one resonant chamber is configured to be at least partially integrally formed with the casing.

6. A noise-reducing gas passage device comprising a resonant chamber, configured to generate pressurized gas and continuously deliver it to a patient's respiratory tract, the noise-reducing gas passage device comprising:

a casing, configured to include at least three chambers comprising at least one resonant chamber, an air intake, and an air outlet, wherein the air intake is configured to receive gas and the air outlet is configured to exhaust the pressurized gas; and the at least one resonant chamber is empty, including walls surrounding the at least one resonant chamber, wherein at least one wall of the at least one resonant chamber includes at least one opening configured to be in communication with other chambers of the at least three chambers other than the at least one resonant chamber;

wherein, the communication between the at least one resonant chamber and the other chambers other than the at least one resonant chamber is formed by a neck, the neck including a first end part connectable to the at least one opening of the at least one resonant chamber and a second end part connectable to the other chambers other than the at least one resonant chamber;

wherein airflow entering the neck is no more than 20% of airflow entering the air intake of the casing; and wherein, from top to bottom, the noise-reducing gas passage device sequentially comprises a first chamber of the at least three chambers, a second chamber of the at least three chambers, and the resonant chamber of the at least three chambers.

7. The noise-reducing gas passage device according to claim 6, wherein the noise-reducing gas passage device includes a blower that is configured to provide the pressurized gas, wherein the blower is provided within the other chambers other than the at least one resonant chamber, wherein the blower has an inlet, and wherein an axis of the inlet of the blower is parallel to a central line of the neck.

8. The noise-reducing gas passage device according to claim 6, wherein the noise-reducing gas passage device includes multiple resonant chambers.

9. The noise-reducing gas passage device according to claim 6, wherein cross-sections of the neck are the same at a same angle from the first end part to the second end part.

10. The noise-reducing gas passage device according to claim 6, wherein the noise-reducing gas passage device includes multiple necks to communicate the at least one resonant chamber with the other chambers other than the at least one resonant chamber.

11. The noise-reducing gas passage device according to claim 6, wherein the casing of the noise-reducing gas passage device includes one of the one of the following materials: polypropylene, polycarbonate, poly (ethylene terephthalate)-1,4-cyclohexanedimethanol ester, polyamide, or polyetheretherketone.

12. A noise-reducing gas passage device comprising a resonant chamber, configured to generate pressurized gas and continuously deliver it to a patient's respiratory tract, the noise-reducing gas passage device comprising:

a casing, configured to include at least two chambers comprising at least one resonant chamber, an air intake, and an air outlet, wherein the air intake is configured to receive gas and the air outlet is configured to exhaust the pressurized gas; and the at least one resonant chamber is empty, including walls surrounding the at least one resonant chamber, wherein at least one wall of the at least one resonant chamber includes at least one opening configured to be in communication with other chambers of the at least two chambers other than the at least one resonant chamber;

wherein, the communication between the at least one resonant chamber and the other chambers other than the at least one resonant chamber is formed by a neck, the neck including a first end part connectable to the at least one opening of the at least one resonant chamber and a second end part connectable to the other chambers other than the at least one resonant chamber;

wherein, an airflow within the other chambers other than the at least one resonant chamber forms a main airflow path, and an angle between a tangent of the main airflow path at the second end part and a central line of the neck is equal to or greater than 30°;

wherein, from top to bottom, the noise-reducing gas passage device sequentially comprises a first chamber of the at least two chambers and a second chamber of the at least two chambers; and wherein the first chamber is configured to accommodate a blower.

13. The noise-reducing gas passage device according to claim 12, wherein the walls of the at least one resonant chamber include one or more of the following materials: plastic, foam, silicone.

14. The noise-reducing gas passage device according to claim 12, wherein a cross-section of the neck is circular or elliptical.

15. The noise-reducing gas passage device according to claim 14, wherein a diameter of the circular cross-section of the neck or a major axis of the elliptical cross-section of the neck is equal to or greater than 0.5 mm.

16. The noise-reducing gas passage device according to claim 15, wherein an area of the cross-section of the neck is at least 0.19625 $mm^2$.

17. The noise-reducing gas passage device according to claim 12, wherein the other chambers other than the at least one resonant chamber include a noise-reducing component.

18. The noise-reducing gas passage device according to claim 17, wherein a form of the noise-reducing component is such that the other chambers other than the at least one resonant chamber have multiple walls of a same form spaced at a certain distance apart.

19. The noise-reducing gas passage device according to claim 12, wherein a material of the walls of the at least one resonant chamber includes a rigid material.

20. A noise-reducing gas passage device comprising a resonant chamber, configured to generate pressurized gas and continuously deliver it to a patient's respiratory tract, the noise-reducing gas passage device comprising:

a casing, configured to include at least two chambers comprising at least one resonant chamber, an air intake, and an air outlet, wherein the air intake is configured to receive gas and the air outlet is configured to exhaust the pressurized gas; and the at least one resonant chamber is empty, including walls surrounding the at least one resonant chamber, wherein only one of the walls of the at least one resonant chamber includes at least one opening configured to be in communication with other chambers of the at least two chambers other than the at least one resonant chamber;

wherein, the communication between the at least one resonant chamber and the other chambers other than the at least one resonant chamber is formed by a neck, the neck including a first end part connectable to the at least one opening of the at least one resonant chamber and a second end part connectable to the other chambers other than the at least one resonant chamber;

wherein, from top to bottom, the noise-reducing gas passage device sequentially comprises a first chamber of the at least two chambers and a second chamber of the at least two chambers, wherein the first chamber is configured to accommodate a blower, and wherein the at least one resonant chamber abuts the air intake and/or is provided opposite an inlet of the blower.

21. The noise-reducing gas passage device according to claim 20, wherein the neck is formed by a wall thickness at a connection point between the at least one resonant chamber and the other chambers other than the at least one resonant chamber.

22. The noise-reducing gas passage device according to claim 20, wherein a total volume of the at least one resonant chamber is greater than or equal to 785 $mm^3$.

23. The noise-reducing gas passage device according to claim 20, wherein the noise-reducing gas passage device includes multiple resonant chambers, and the multiple resonant chambers are provided at different locations.

24. The noise-reducing gas passage device according to claim 20, wherein the walls of the at least one resonant chamber include one of the following materials: polypropylene, polycarbonate, poly (ethylene terephthalate)-1,4-cyclohexanedimethanol ester, polyamide, or polyetheretherketone.

25. The noise-reducing gas passage device according to claim 20, wherein an area of the at least one opening of the at least one resonant chamber is greater than or equal to 0.19625 $mm^2$.

* * * * *